United States Patent [19]

Inoue et al.

[11] Patent Number: 4,933,265
[45] Date of Patent: * Jun. 12, 1990

[54] PROCESS FOR FORMING DIRECT POSITIVE COLOR IMAGE

[75] Inventors: Noriyuki Inoue; Tatsuo Heki; Tetsuro Kojima; Shinji Ueda, all of Kanagawa, Japan

[73] Assignee: Fuji Photo Film Co., Ltd., Kanagawa, Japan

[ * ] Notice: The portion of the term of this patent subsequent to Dec. 6, 2002 has been disclaimed.

[21] Appl. No.: 317,142

[22] Filed: Feb. 23, 1989

Related U.S. Application Data

[63] Continuation of Ser. No. 91,928, Sep. 1, 1987, abandoned.

[30] Foreign Application Priority Data

Sep. 1, 1986 [JP] Japan .................................. 61-205343
Dec. 4, 1986 [JP] Japan .................................. 61-289700
Dec. 4, 1986 [JP] Japan .................................. 61-289703

[51] Int. Cl.$^5$ .......................... G03C 5/24; G03C 7/26
[52] U.S. Cl. .................................... 430/378; 430/380; 430/406; 430/409; 430/410; 430/445; 430/489; 430/547; 430/601; 430/607
[58] Field of Search ............... 430/378, 380, 217, 406, 430/409, 410, 411, 445, 489, 547, 601, 607, 598

[56] References Cited

U.S. PATENT DOCUMENTS

| | | | |
|---|---|---|---|
| 3,212,892 | 10/1965 | Konig et al. ......................... | 430/445 |
| 4,276,364 | 6/1981 | Leone .................................... | 430/217 |
| 4,356,258 | 10/1982 | Usui et al. ............................ | 430/389 |
| 4,358,528 | 11/1982 | Takagi et al. ....................... | 430/251 |
| 4,418,140 | 11/1983 | Mifune et al. ....................... | 430/445 |
| 4,444,871 | 4/1984 | Miyaoka et al. ..................... | 430/378 |
| 4,467,029 | 8/1984 | Nishide et al. ...................... | 430/445 |
| 4,471,044 | 9/1984 | Parton et al. ........................ | 430/611 |
| 4,481,285 | 11/1984 | Takagi et al. ....................... | 430/598 |
| 4,524,129 | 6/1985 | Kishimoto et al. ................. | 430/445 |
| 4,533,625 | 8/1985 | Ichijima et al. ..................... | 430/522 |
| 4,610,954 | 9/1986 | Torigoe et al. ...................... | 430/445 |
| 4,636,457 | 1/1987 | Valbusa et al. ...................... | 430/375 |
| 4,789,627 | 12/1988 | Inoue et al. .......................... | 430/406 |
| 4,801,520 | 1/1989 | Inoue et al. .......................... | 430/378 |
| 4,863,839 | 9/1989 | Heki et al. ............................ | 430/406 |

Primary Examiner—Roland E. Martin
Assistant Examiner—P. A. Doody
Attorney, Agent, or Firm—Sughrue, Mion, Zinn, Macpeak & Seas

[57] ABSTRACT

A process for forming a direct positive color image is disclosed, the process comprising imagewise exposing a photosensitive material containing at least one emulsion layer of silver halide of internal latent image type, which has not been preliminarily fogged, and a color image-forming coupler; developing said material using a surface developing solution containing an aromatic primary amine color developing agent in the presence of a nucleating agent and/or in the condition that fogging exposure is carried out prior to the developing step or during the developing step; bleaching; and fixing, wherein said color coupler is a compound which is in itself substantially nondiffusible, and capable of forming or releasing a substantially nondiffusible dye upon oxidative coupling with said aromatic primary amine color developing agent and said development processing is carried out at a pH of 11.5 or less using a developing solution containing substantially no benzyl alcohol in the presence of at least one compound selected from the group consisting of the compounds represented by the general formula (I)

$$A\mathrm{-}(Y^1\mathrm{-}_{\overline{n}}R)_m$$

6 Claims, No Drawings

PROCESS FOR FORMING DIRECT POSITIVE COLOR IMAGE

This is a division of application Ser. No. 07/091,928, filed Sept. 1, 1987, now abandoned.

FIELD OF THE INVENTION

This invention relates to a process for direct positive color image which comprises subjecting direct positive silver halide photosensitive material to color development processing in the presence of a nucleating agent and/or carrying out fogging exposure, after an imagewise exposure to light.

BACKGROUND OF THE INVENTION

There is well known a photographic process which can obtain a direct positive image without the need of reversal processing step or a negative film.

The conventionally known processes which form positive images by the use of direct positive silver halide photosentitive materials, when considering their usefulness in practice, excluding very special ones, may be divided into the following two main types.

In one of these types, use is made of a silver halide emulsion which has been preliminarily fogged, and by destroying the fogged nuclei (latent image) in the exposed area by taking advantage of solarization or Hershel effect one can obtain a direct positive image after the development.

In another type, one can obtain a direct positive image by subjecting a silver halide emulsion of internal latent image type which has not been fogged, to surface development processing after the fogging treatment or during the fogging treatment after the imagewise exposure.

The term "silver halide emulsion of internal latent image type" as used herein means a silver halide emulsion of such a type that photosensitive nuclei are contained mainly in the interior of the silver halide grains, and so latent image is mainly formed in the interior of the grains by exposure.

As compared with the process of the former type, the process of the latter type is in general high in the photographic sensitivity, so that it is adapted for the use requiring a high photographic speed, and this invention relates to the latter type.

In this technical field, hitherto, various techniques have been known, and the chief of them are described in the specifications of U.S. Pat. Nos. 2,592,250, 2,466,957, 2,497,875, 2,588,982, 3,317,322, 3,761,266, 3,761,276, 3,796,577, and British Pat. Nos. 1,151,363, 1,150,553, 1,011,062, etc.

In accordance with these prior-known processes there are obtainable photosensitive materials which have comparatively high photographic speed as the direct positive type.

Also, further particulars concerning the mechanism of the formation of a direct positive image are described, for instance, in T. H. James: "The Theory of the Photographic Process" 4th Ed., Chapter 7, pp. 182 to 193, U.S. Pat. No. 3,761,276, etc. According to these descriptions it is believed that by the action of the surface desensitization due to the so-called internal latent image which was formed in the interior of the silver halide by the first exposure through a pattern, only the surfaces of the silver halide grains in the unexposed area are allowed to form selectively fogged nuclei, and then by carrying out the ordinary, so-called surface development processing a photographic image (direct positive image) is formed in the unexposed area.

As the means for forming selectively fogged nuclei as above described, there are known a process, called generally "a light fogging method", in which the second exposure is given all over the surface of the photosensitive layer (for instance, British Pat. No. 1,151,363) and process, called "a chemical fogging method", using a nucleating agent. With regard to the latter method there is a description for instance in Research Disclosure vol. 151, No. 15162 (November, 1976), pp. 76 to 78.

Formation of a direct positive color image may be achieved by subjecting a silver halide photosensitive material of internal latent image type to surface color development processing either after the fogging treatment or during the fogging treatment, and thereafter, by bleaching and fixing (or blix) treatments, followed by ordinary water wash and/or stabilization treatment.

The light fogging method has disadvantages such that the performance of the finished products of the photosensitive material is liable to vary depending on the variations of the exposure, time of development, composition of developing solution, processing temperature, etc. and moreover, the method requires a long time of development, and is difficult to obtain high maximum density.

On the other hand, the chemical fogging method has disadvantages in that since the speed of development is low when the pH of the developing solution is low, the pH should be made high, but as the developing agent is readily deteriorated by aerial oxidation when pH is high, the fogging effect is reduced.

As above-described the conventional fogging methods were both difficult to obtain stabilized and satisfactory direct positive images. As the means for solving such a problem there were proposed compounds which can exhibit nucleating action even at a pH of 12 or less in Japanese Patent Application (OPI) No. 69613/77 (the term "OPI" as used herein means an "Unexamined Published Application"), U.S. Pat. Nos. 3,615,615 and 3,850,638. These nucleating agents however have the defects such that they either act upon the silver halide or decompose themselves during the storage of the photosensitive materials prior to the processing, and eventually the maximum density after the processing is lowered.

In U.S. Pat. No. 3,227,552 it is described that the speed of development at a moderate density can be raised by the use of hydroquinone derivatives. But, even by their use the speed of development was not sufficient, and especially at a pH of 12 or less no sufficient speed could be obtained.

Also, in Japanese Patent Application (OPI) No. 170843/85 it is described that by the addition of mercapto compounds having a carboxylic group or a sulfonic acid group the maximum density can be attained. But, even by the addition of these compounds the maximum density cannot be fully improved. Moreover, the pH of the developing solution is 12.0 indicating insufficient stability of the developing solution.

Japanese Patent Application (OPI) No. 134848/80 described that by treating with a processing solution (pH 12.0) containing a tetraazaindene series compound in the presence of a nucleating agent the minimum density is lowered so as to prevent the formation of the second reversal negative image. But, in this process, the maximum density cannot be high, and the speed of development also cannot be fast.

Further, Japanese Patent Publication No. 12709/70 describes that a triazoline-thion or tetraazoline-thione series compound is added as an antifoggant to the photosensitive material forming a direct positive image by the light fogging method. But, even by these methods high maximum density and fast speed of development could not be attained.

Thus, none of the techniques have hitherto been able to obtain a direct positive color image which has a high maximum density and a low minimum density in a stabilized state by a short time of processing using a developing solution having a low pH (pH 12 or less).

On the other hand, in order to accelerate the speed of development and color development of a color developing solution, there have hitherto been proposed various methods. In these methods, in order that the developing agent may form a dye by coupling with a coupler, it is essential that the color developing agent itself is held in the dispersed oil drops of the coupler, and as the additives for increasing the rate of its penetration and promoting the color development various kinds of additives are known. Especially, benzyl alcohol is best known as an additive having a large effect upon such promotion of color development, and so it has hitherto been used in various color photographic materials, and it is still at present widely in use.

Benzyl alcohol is in some degree soluble in water, but not easily soluble, so that in order to enhance the solubility diethylene glycol, triethylene glycol or alkanolamine is usually added to benzyl alcohol.

However, in the above-described compounds and the benzyl alcohol itself also, the environmental pollution load is large in the disposal of waste water since the BOD or COD value becomes high, and therefore, as tobenzyl alcohol, its reduction or removal has been expected from the standpoint of the waste water disposal in spite of its mertis in the improvement in color development, solubility, etc.

Furthermore, even when in use of solvents such as the above-described diethylene glycol or the like the solubility of benzyl alcohol was not sufficient to such an extent that it caused to take much labor and time for the preparation of the developing solution.

Still further, when benzyl alcohol is brought into the subsequent bath, which may be a bleaching bath or a bleach-fix bath together with the developing solution, and as the result it accumulates therein, a leuco body is formed depending on the kind of cyan dyes, causing a decrease in the color developing density. In addition to the above, as the accumulation of benzyl alcohol further makes insufficient the washing out of the components of the developing solution, especially of color developing solution, it was found that the components thus remaining cause the deterioration of the storage stability of images.

From these viewpoints, the reduction or removal of benzyl alcohol from developing solution is being keenly desired.

In the present color labo industry these problems are not as yet solved on the one hand, and because of the strong request for the shortened delivery time of finished print, the time of processing is under the necessity of being shortened on the other hand.

It is, however, very obvious that if the time of development is shortened using a color developing solution from which benzyl alcohol has been removed the color developing density remarkably lowers, so that the prior art can never fulfil all the requirements simultaneously.

The direct positive color photosensitive material is also liable to be affected by the variation of the pH of color developing agent as compared with the ordinary negative color photosensitive material. Especially when a color developing solution containing no benzyl alcohol is used in the processing, the lowering of the maximum density due to lowering of pH is marked.

It was also found that when the direct positive color photosensitive material is stored under the condition of high temperature and high humidity prior to the development, the maximum density is liable to lower.

Also, the direct positive color photosensitive material produces the second reversal (re-reversal) negative image by high intensity exposure. Especially when a color developing solution containing no benzyl alcohol is used in the processing, such a tendency is more pronounced, and also, when a color developing solution deteriorated by running is used in the processing, a marked lowering occurs.

In addition, the direct positive color photosensitive material shows a defect in that the grains of the color image are liable to become coarse as compared with the photosensitive material using the ordinary emulsion of negative type. Especially such a defect is more pronounced when a color developing solution containing nobenzyl alcohol is used in the processing, when the photosensitive material has been stored for a long period of time, or when a color developing solution has been fatigued by running.

SUMMARY OF THE INVENTION

Thus, the object of this invention is to provide a process for direct formation of positive color image, of which color developing density lowers in a lesser degree even when a short time of processing is carried out using a color developing solution containing no benzyl alcohol, and in particular to provide a color photosensitive material which can achieve an efficient color development even under the above-described conditions, as well as to provide a process for direct formation of positive color image by the use of such a photosensitive material.

Another object of this invention is to provide a process for direct formation of positive color image, of which the maximum density is hardly variable even when the pH of the color developing solution containing no benzyl alcohol varies.

Still another object of this invention is to provide a process for direct formation of positive color image, which is of high image quality such that the grains do not become coarse even when a color developing solution containing no benzyl alcohol is used in the processing, when the photosensitive material which has been stored for a long period of time is used, or when the color developing solution which is fatigued by running is used in the processing.

Further the object of this invention is to provide a process for direct formation of positive color image by the use of a photosensitive material having good storage stability.

It is also the object of this invention to provide a process for direct formation of positive color image, in which the second reversal (re-reversal) negative image is rarely produced when a color developing solution containing no benzyl alcohol is used in running treatment.

DETAILED DESCRIPTION OF THE INVENTION

It was found that the above-described objects of this invention could be effectively achieved by the following process: that is, "A process for forming direct positive color image comprising imagewise exposing a photosensitive material containing at least one emulsion layer of silver halide of internal latent image type, which has not been preliminarily fogged, and a color image-forming coupler, developing said exposed material using a surface developing solution containing an aromatic primary amine color developing agent, in the presence of a nucleating agent and/or in the condition that fogging exposure in carried out prior to the developing step or during the developing step; bleaching and fixing said developed material, wherein said color coupler is a compound which is in itself substantially nondiffusible, and moreover, capable of forming or releasing a substantially nondiffusible dye upon oxidative coupling with said aromatic primary amine color developing agent, and said development processing is carried out at a pH of 11.5 or less using a developing solution containing substantially no benzyl alcohol in the presence of at least one compound (i.e., nucleation promoter) selected from the group consisting of the compounds represented by the later described general formula I."

Herein the expression "substantially no benzyl alcohol" means that benzyl alcohol is contained in an amount of 2 ml or less, or preferably 0.5 ml or less per liter of the developing solution, or more preferably, it is not contained entirely.

The expression "substantially nondiffusible dye" means that dye is nondiffusible or diffusible in a degree not to effect on photographic performances.

Further, the term "a nucleating agent" means a substance which functions to form a direct positive image when an emulsion of silver halide of internal latent image type which has not been preliminarily fogged, is subjected to surface development processing.

Also, the term "a nucleation promoter" means a substance, which is in itself substantially incapable of functioning as the above-described nucleating agent, but can act as a promoter of the action of a nucleating agent by hightening the maximum density of a positive image and/or by quickening the time of development required for a direct positive image to each a definite density. These nucleation promoters can be used in combination of two or more thereof.

The nucleation promoters useful in this invention are represented by the following general formula (I).

General formula (I-a)

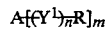

wherein A represents a group being adsorbed on silver halide.

Examples of compounds having a group A being adsorbed on silver halide include compounds having a mercapto group attached to a heterocyclic ring, heterocyclic compounds capable of forming iminosilver, and hydrocarbons having a mercapto group.

Examples of compounds having a mercapto group attached to a heterocyclic ring include substituted or unsubstituted mercaptoazoles such as a mercaptotetrazole, a mercaptotriazole, a mercaptoimidozole, a mercaptothiadiazole, a mercaptooxadiazole, a mercaptoselenadiazole, a mercaptooxazole, a mercaptothiazole, a mercaptobenzoxazole, a mercaptobenzimidazole, a mercaptobenzthiazole, etc., (e.g., 5-mercaptotetrazoles, 3-mercapto-1,2,4-triazoles, 2-mercaptoimidazoles, 2-mercapto-1,3,4-thiadiazoles, 5-mercapto-1,2,4-thiadiazoles, 2-mercapto-1,3,4-oxadiazoles, 2-mercapto-1,3,4-selenadiazoles, 2-mercaptooxazoles, 2-mercaptothiazoles, 2-mercaptobenzoxazoles, 2-mercaptobenzimidazoles, 2-mercaptobenzthiazoles, etc.), substituted or unsubstituted mercaptopyrimidines (e.g., 2-mercaptopyrimidines, etc.), etc.

Examples of heterocyclic compounds capable of forming iminosilver include respectively substituted or unsubstituted indazoles, benzimidazoles, benzotriazoles, benzoxazoles, benzthiazoles, imidazoles, thiazoles, oxazoles, triazoles, tetrazoles, azaindenes, pyrazoles, indoles, etc.

Substituents substituted on a mercapto group attached to a heterocyclic ring and on a heterocyclic compound capable of forming iminosilver include the same as those substituted on a heterocyclic ring composing a compound represented by the general formula (II).

Examples of hydrocarbons having a mercapto group include alkylmercaptanes, arylmercaptanes, alkenylmercaptanes, aralkylmercaptanes, etc., wherein the alkyl moiety has 1 to 12 carbon atoms, the aryl moiety has 6 to 12 carbon atoms and the alkenyl moiety has 2 to 12 carbon atoms.

$Y^1$ represents a divalent group consisting of an atom or atomic group selected from the group consisting of nitrogen atom, carbon atom, nitrogen atom, oxygen atom, and sulfur atom. The examples of the divalent connecting group include

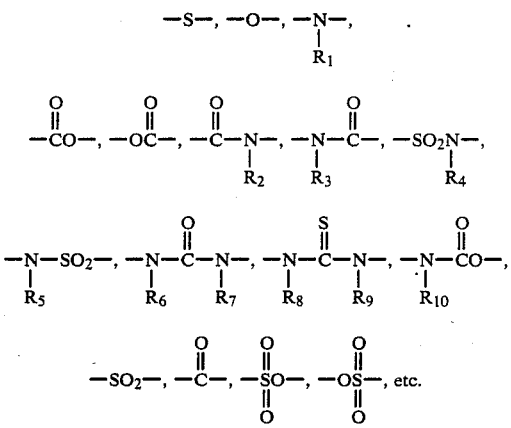

$R_1$, $R_2$, $R_3$, $R_4$, $R_5$, $R_6$, $R_7$, $R_8$, $R_9$, and $R_{10}$ represent a hydrogen atom, respectively substituted or unsubstituted alkyl groups preferably having 1 to 12 carbon atoms (e.g., methyl, ethyl, propyl, n-butyl, etc.), substituted or unsubstituted aryl groups preferably having 6 to 12 carbon atoms (e.g., phenyl, 2-methyl-phenyl, etc.), substituted or unsubstituted alkenyl groups preferably having 3 to 12 carbon atoms (e.g. propenyl, 1-methylvinyl, etc.), or substituted or unsubstituted aralkyl groups preferably having 7 to 12 carbon atoms (e.g., benzyl, phenetyl, etc.).

R represents a polar substituent group or an organic group containing at least one of a thioether group preferably having 2 to 12 carbon atoms, an amino group preferably having 1 to 12 carbons atoms (including salts thereof), an ammonium group, an ether group preferably having 2 to 12 carbon atoms, and heterocyclic group (including salts thereof). As these organic groups there may be mentioned those which are obtained by combining a group selected from respectively substituted or unsubstituted alkyl group preferably 1 or 12 carbon atoms, alkenyl group preferably 2 or 12 carbon atoms, aralkyl group preferably 7 or 12 carbon atoms, aryl groups having 6 to 12 carbon atoms with the above-described groups, or further combinations of these organic groups. Specific examples of such groups include a dimethylaminoethyl group, an aminoethyl group, a diethylaminoethyl group, a dibutylaminoethyl group, a dimethylaminopropyl hydrochloride, a dimethylaminoethylthioethyl group, a 4-dimethylaminophenyl group, a 4-dimethylaminobenzyl group, a methylthioethyl group, an ethylthiopropyl group, a 4-methylthio-3-cyanophenyl group, a methylthiomethyl group, a trimethylammonioethyl group, a methoxyethyl group, a methoxyethoxyethoxyethyl group, a methoxyethylthioethyl group, a 3,4-dimethoxyphenyl group, a 3-chloro-4-methoxyphenyl group, a morpholinoethyl group, a 1-imidazolylethyl group, a morpholinoethylthioethyl group, a pyrrolidinoethyl group, a piperidinopropyl group, a 2-pyridylmethyl group, 2-(1-imidazolyl)ethylthioethyl group, a pyrazolylethyl group, a triazolylethyl group, a methoxyethoxyethoxyethoxycarbonyl-aminoethyl group, etc.

The polar substituent group preferably includes a hydrogen atom, a halogen atom (e.g., chlorine atom, bromine atom, etc.), a hydroxy group, a nitro group, a cyano group, respectively substituted or unsubstituted sulfonyl groups (e.g., methanesulfonyl, ethanesulfonyl, p-toluenesulfonyl, etc.), carbamoyl groups (e.g., unsubstituted carbamoyl, methylcarbamoyl, etc.), sulfamoyl groups (e.g., unsubstituted sulfamoyl, methylsulfamoyl group, etc.), carbonamido (carboxylic acid amido) groups (e.g., acetamido, benzamido, etc.), sulfonamido groups (e.g., methanesulfonamido, benzenesulfonamido, etc.), acyloxy group (e.g., acetyloxy, benzoyloxy, etc.), ureido groups (e.g., unsubstituted ureido, methylureido, ethylureido, etc.), acyl groups (e.g., acetyl, benzoyl, etc.), thioureido groups (e.g., unsubstituted ureido, methylureido, etc.), sulfonyloxy groups (e.g., methanesulfonyloxy, p-toluenesulfonyloxy, etc.), oxycarbonyl groups (e.g., methoxycarbonyl, phenoxycarbonyl, etc.), oxysulfonyl groups (e.g., methoxysulfonyl, phenoxysulfonyl, ethoxysulfonyl, etc.), oxycarbonylamino groups (e.g., ethoxycarbonylamino, phenoxycarbonylamino, etc.), or a mercapto group.

n represents 0 or 1, and m represents 1 or 2.

Substituents substituted on the alkyl group, the aryl group, the alkenyl group and the aralkyl described above include the same as substituents on a heterocyclic ring composing a compound represented by the general formula (II).

Of the compounds represented by the general formula (I), the following compounds represented by the general formulas (II) and (III) are preferable.

General Formula (II)

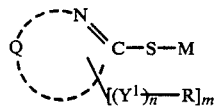

In the general formula (II), Q represents preferably an atomic group required for the formation of a 5- or 6-membered heterocyclic ring containing at least one atom selected from the group consisting of carbon atom, nitrogen atom, oxygen atom, sulfur atom, and selenium atom. This heterocyclic ring may be such a one condensed with a aromatic or heterocyclic ring.

Examples of heterocyclic rings include tetrazoles, triazoles, imidazoles, thiadiazoles, oxadiazoles, selenadiazoles, oxazoles, thiazoles, benzoxazoles, benzthiazoles, benzimidazoles, pyrimidines, etc.

M represents a hydrogen atom, an alkali metal atom (e.g., sodium atom, potassium atom, etc.), an ammonium group, such as an alkylammonium group, an alkaryl ammonium group, an aryl ammonium group, etc., wherein each alkyl group has 0 to 12 carbon atoms and each aryl group has 0 or 6 to 12 carbon atoms, (e.g., trimethylammonium, dimethylbenzalammonium, etc.), and a group which can be replaced by H or an alkali metal atom under an alkaline condition such as an acyl group preferably having 2 to 12 carbon atoms, a sulfonylalkyl group preferably having 3 to 12 carbon atoms, a cyanoalkyl group preferably having 3 to 12 carbon atoms, etc., (e.g., acetyl, cyanoethyl, methane sulfonylethyl, etc.)

These heterocyclic rings may also be substituted by a nitro group, a halogen atom, (e.g., chlorine atom, bromine atom, etc.), a mercapto group, a cyano group, respectively substituted or unsubstituted alkyl groups preferably having 1 to 12 carbon atoms (e.g., methyl, ethyl, propyl, t-butyl, cyanoethyl, etc.), wherein the preferable substituent for the alkyl group includes an acyloxy group, a sulfonyl group, a sulfonyloxy group, a carbamoyl group, an ureido group, a sulfamoyl group, a thioureido group, a carbonamido group, an oxycabonyl group, a sulfonamido group, a cyano group and a halogen atom, aryl groups preferably having 6 to 12 carbon atoms (e.g., phenyl, 4-methanesulfonamidophenyl, 4-methylphenyl, 3,4-dichlorophenyl, naphthyl, etc.), alkenyl group preferably having 2 to 12 carbon atoms (e.g., allyl, etc.), aralkyl groups preferably having 7 to 12 carbon atoms (e.g., benzyl, 4-methylbenzyl, phenetyl, etc.), sulfonyl groups preferably having 0 to 12 carbon atoms (e.g., methanesulfonyl, ethanesulfonyl, p-toluenesulfonyl, etc.), carbamoyl groups preferably having 1 to 12 carbon atoms (e.g., unsubstituted carbamoyl, methylcarbamoyl, phenylcarbamoyl, etc.), sulfamoyl groups preferably having 0 to 12 carbon atoms (e.g., unsubstituted sulfamoyl, methylsulfamoyl, phenylsulfamoyl, etc.), carboxylic acid amido groups preferably having 2 to 12 carbon atoms (e.g., acetamido, benzamido, etc.), sulfonamido groups preferably having 1 to 12 carbon atoms (e.g., methanesulfonamido, benzenesulfonamido, p-toluenesulfonamido, etc.), acyloxy groups preferably having 2 to 12 carbon atoms (e.g., acetyloxy, benzoyloxy, etc.), sulfonyloxy groups preferably having 1 to 12 carbon atoms (e.g., methanesulfonyloxy, etc.), Ureido groups preferably having 1 to 12 carbon atoms, (e.g., unsubstituted ureido, methylureido, ethylureido, phenylureido, etc.), thioureido groups preferably having 1 to 12 carbon atoms, (e.g., unsubstituted thioureido, methylthioureido, etc.), acyl groups preferably having 2 to 12 carbon atoms, (e.g., acetyl, benzoyl, etc.), oxycarbonyl groups preferably having 2 to 12 carbon atoms, (e.g., methoxycarbonyl, phenoxycarbonyl, etc.), oxycarbonylamino groups preferably having 2 to 12 carbon atoms, (e.g., methoxycarbonylamino, phenoxycarbonylamino, 2-ethylhexyloxycarbonylamino, etc.), carboxylic acids or salts thereof preferably having 1 to 12 carbon atoms, sulfonic acids or salts thereof, a hydroxyl group, etc., but from the viewpoint of the effect of promoting the nucleation it is preferable that heterocyclic rings are not substituted by carboxylic acides or salts thereof, sulfonic acids or salts thereof, or a hydroxyl group.

Preferable examples of heterocyclic rings represented by Q include tetrazoles, triazoles, imidazoles, thiadiazoles, oxadiazoles, etc.

$Y^1$, R, m, and n are respectively the same as defined in general formula (I).

General formula (III)

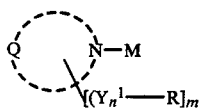

In the above formula, $Y^1$, R, m, n, Q, and M are the same as defined in General formulas (I) and (II).

Examples of heterocyclic rings formed by Q preferably include indazoles, benzimidazoles, benzotriazoles, benzoxazoles, benzthiazoles, imidazoles, thiazoles, oxazoles, triazoles, tetrazoles, tetraazaindenes, triazaindenes, diazaindenes, pyrazoles, indoles, etc.

Of the compounds represented by the general formula (II), the preferable compounds include compounds represented by the following general formulas (IV), (V), (VI) and (VII).

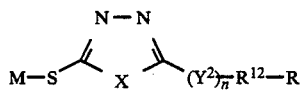
General formula (IV)

In the above formula, M represents a hydrogen atom, an alkali metal atom, an ammonium group, or a group which can cleave under an alkaline condition. X represents an oxygen atom, a sulfur atom or a selenium atom.

$Y^2$ represents

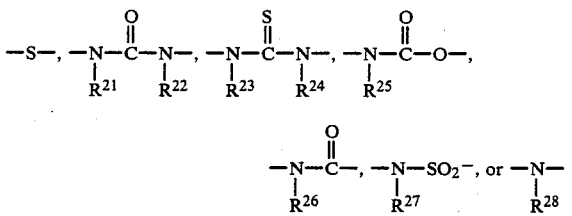

In these formulas, $R_{21}$, $R_{22}$, $R_{23}$, $R_{24}$, $R_{25}$, $R_{26}$, $R_{27}$, and $R_{28}$ represents a hydrogen atom, respectively substituted or unsubstituted alkyl groups preferably having 1 to 12 carbon atoms (e.g., methyl, ethyl, propyl, etc.), substituted or unsubstituted aryl groups preferably having 6 to 12 carbon atoms (e.g., phenyl, 2-methylphenyl, etc.), substituted or unsubstituted alkenyl groups preferably having 3 to 12 carbon atoms (e.g., propenyl, 1-methylvinyl, etc.), or substituted or unsubstituted aralkyl groups preferably having 7 to 12 carbon atoms (e.g., benzyl, phenetyl, etc.). Substituents substituted on the alkyl group, the aryl group, the alkenyl group and the aralkyl group include the same as substitents on a heterocyclic ring composing a compound represented by the general formula (II).

$R^{12}$ represents straight or branched alkylene groups preferably having 1 to 12 carbon atoms (e.g., methylene, ethylene, propylene, butylene, hexylene, 1-methylethylene, etc.), straight or branched alkenylene groups preferably having 2 to 12 carbon atoms (e.g., vinylene, 1-methylvinylene, etc.), straight or branched aralkylene groups preferably having 7 to 12 carbon atoms (e.g., benzylidene, etc.), or arylene groups preferably having 6 to 12 carbon atoms (e.g., phenylene, naphthylene, etc.). The above-described groups represented by $R^{12}$ may be further substituted. R represents the same as those previously defined.

n represents 0 or 1.

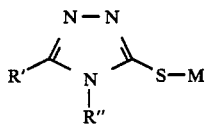
General formula (V)

In the above formula, R' represents a hydrogen atom, a halogen atom (e.g., chlorine atom, bromine atom, etc.), a nitro group, a mercapto group, or a $-(Y^3)_{n'}R^{11}R$ group. R" represents a hydrogen atom or a $-(Y^4)_{m'}R^{11}$ R group. At least one of R' and R" represents $-(Y^3)_{n'}R^{11}R$ group and $-(Y^4)_{m'}R^{11}$—R group, respectively. $Y^3$ and $Y^4$ represent

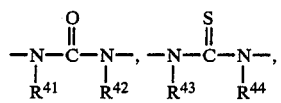

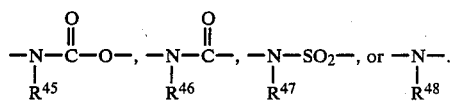

m' represents 0 or 1.

M represents a hydrogen atom, an alkali metal atom, an ammonium group, or a group which can cleave under an alkaline condition. $R^{41}$, $R^{42}$, $R^{43}$, $R^{44}$, $R^{45}$, $R^{46}$, $R^{47}$, and $R^{48}$, represent a hydrogen atom, respectively substituted or unsubstituted alkyl groups preferably having 1 to 12 carbon atoms, (e.g., methyl, ethyl, propyl, etc.), substituted or unsubstituted aryl groups preferably having 6 to 12 carbon atoms (e.g., phenyl, 2-methoylphenyl, etc.), substituted or unsubstituted alkenyl groups preferably having 2 to 12 carbon atoms (e.g., propenyl, methylvinyl, etc.), or substituted or unsubstituted aralkyl groups preferably having 7 to 12 carbon atoms (e.g., benzyl, phenethyl, etc.). $R^{11}$ represents straight or branched alkylene groups preferably having 1 to 12 carbon atoms, (e.g. methylene, ethylene, propylene, butylene, hexylene, 1-methylethylene, etc.), straight or branched alkenylene groups preferably having 2 to 12 carbon atoms, (e.g., vinylene, 1-methylvinylene, etc.), straight or branched aralkylene groups preferably having 7 to 12 carbon atoms, (e.g., benzylidene, etc.), or arylene groups preferably having 6 to 12 carbon atoms (e.g., phenylene, naphthylene, etc.). Substituents for the above groups include the same as those substituted on a heterocyclic ring composing a compound represented by the general formula (II). The above-described groups represented by $R^{11}$ may be further substituted.

Z is the same as defined in general formula (IV).

n' represents 0 or 1.

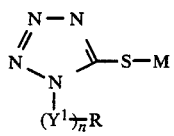

General formula (VI)

In the formula (VI), wherein M, R, $Y^1$ and n are the same as defined in General formulae (I) and (II).

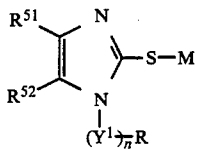

General formula (VII)

In the above formula (VII), $R^{51}$ and $R^{52}$ each represents a hydrogen atom, a halogen atom, a substituted or unsubstituted amino group, a nitro group, a substituted or unsubstituted alkyl group preferably having 1 to 12 carbon atoms, a substituted or unsubstituted alkenyl group preferably having 2 to 12 carbon atoms, a substituted or unsubstituted aralkyl group preferably having 7 to 12 carbon atoms, a substituted or unsubstituted aryl group preferably having 6 to 12 carbon atoms, wherein M, $Y^1$ and n are the same as defined in General Formulae (I) and (II). Substituents for the above groups include the same as those substituted on a heterocyclic ring composing a compound represented by the general formula (II).

In the above-described process the nucleation promoters represented by the general formula (I) and nucleating agents may be allowed to coexist.

Specific compounds will be shown below, but this invention should not be construed as being limited thereto.

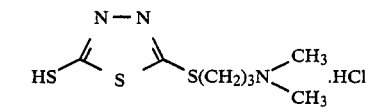 1

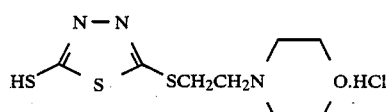 2

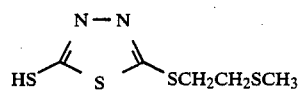 3

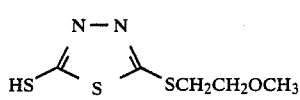 4

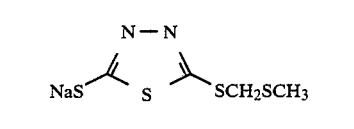 5

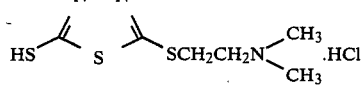 6

-continued

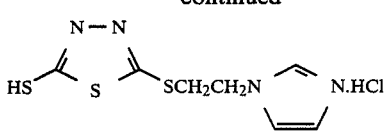 7

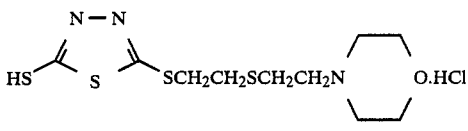 8

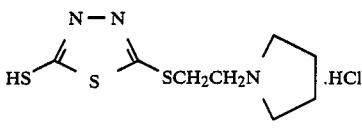 9

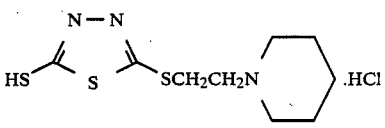 10

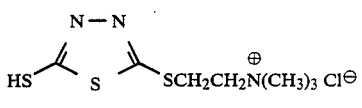 11

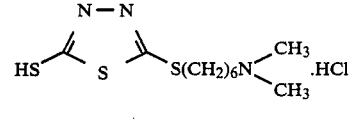 12

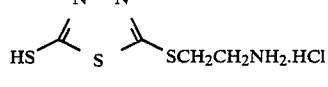 13

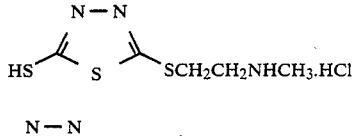 14

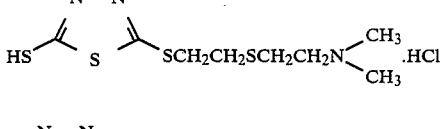 15

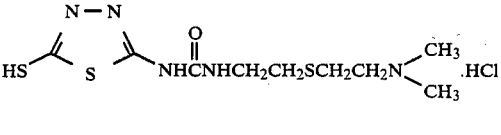 16

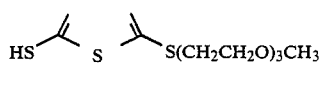 17

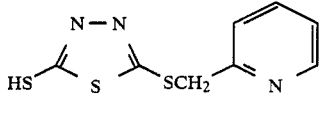 18

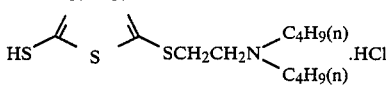 19

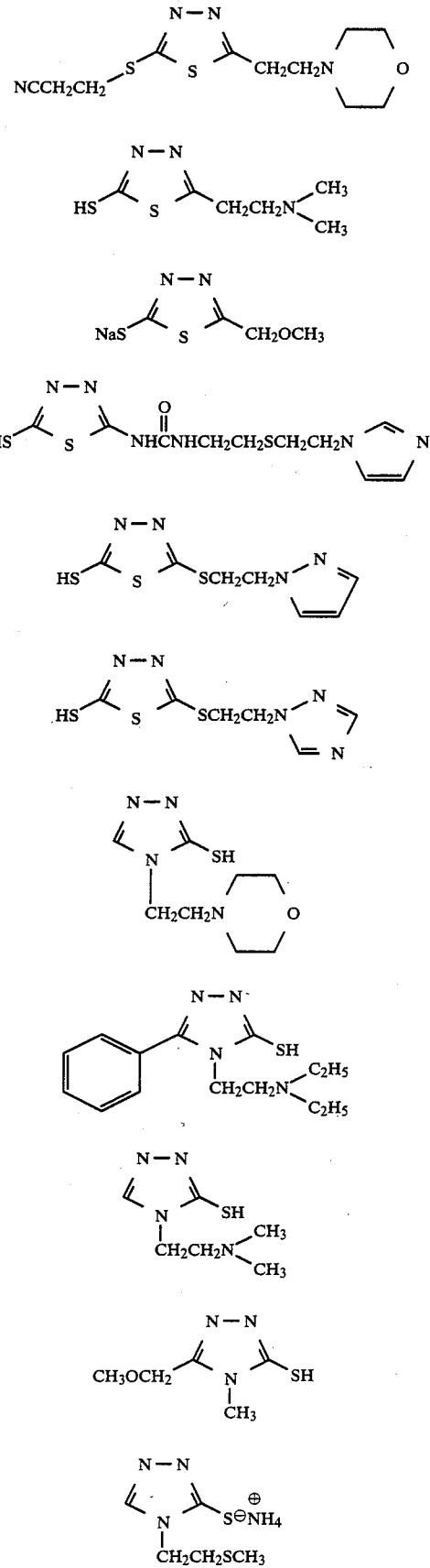

The compounds represented by the general formula (I) used in this invention can be synthesized according to the methods described in the following literature or according to the typical synthesis examples described below.

Literature: Berichte der Deutschen Chemischen Gesellschaft, 28, 77 (1875), Japanese Patent Applications (OPI) Nos. 37436/75, 3231/76; U.S. Pat. Nos. 3,295,976, 3,376,310; Berichte der Deutschen Chemischen Gesellschaft, 22, 568 (1889), ibid., 29, 2483 (1896), J. Chem. Soc., 1932, J. Am. Chem. Soc., 71, 4000 (1949), U.S. Pat. Nos. 2,585,388, 2,541,924; Advances in Heterocyclic Chemistry, 9, 165 (1968), Organic Synthesis, IV, 569 (1963), J. Am. Chem. Soc., 45, 2390 (1923), Chemische Berichte, 9, 465 (1876), Japanese Patent Publication No. 28496/65, Japanese Patent Application (OPI) No. 89034/75, U.S. Pat. Nos. 3,106,467, 3,420,670, 2,271,229, 3,137,578, 3,148,066, 3,511,663, 3,060,028, 3,271,154, 3,251,691, 3,598,599, Japanese Patent Publication No. 4135/68, U.S. Pat. Nos. 3,615,616, 3,420,664, 3,071,465, 2,444,605, 2,444,606, 2,444,607, 2,935,404, etc.

SYNTHESIS EXAMPLE 1

Synthetic method for Illustrative Compound (1)

7.5 g of 2,5-dimercapto-1,3,4-thiadiazole, 7.9 g of 3-dimethylaminopropyl chloride hydrochloride, and 4 g of pyridine were added to 60 ml of n-butanol, and heated for 2 hours at reflux. The reaction liquid was cooled with ice, and the crystals deposited were filtered off, and recrystallized from ethanol. Yield 11 g and melting point 149°–152° C.

SYNTHESIS EXAMPLE 2

Synthetic method for Illustrative Compound (13)

7.5 g of 2.5-dimercapto-1,3,4-thiadiazole, 5.8 g of 2-aminoethyl chloride hydrochloride, and 4 g of pyridine were added to 60 ml of n-butanol, and heated for 2 hours at reflux. The reaction liquid was cooled with ice, and the crystals deposited were filtered off, and recrystallized from methanol/water. Yield 7.1 g and melting point 228–229 (decomposed).

SYNTHESIS EXAMPLE 3

Synthetic method for Illustrative Compound (6)

7.5 g of 2,5-dimercapto-1,3,4-thiadiazole, 7.3 g of 2-dimethylaminoethyl chloride hydrochloride, and 4 g of pyridine were added to 60 ml of n-butanol, and heated from 2 hours at reflux. The reaction liquid was cooled with ice, and the crystals deposited were filtered off, and recrystallized from ethanol. Yield 7.9 g and melting point 161°–163° C.

SYNTHESIS EXAMPLE 4

Synthetic method for Illustrative Compound (7)

15.0 g of 2,5-dimercapto-1,3,4-thiazole, 20.0 g of 1-(2-chloroethyl)imidazole hydrochloride, and 9.5 g of pyridine were added to 100 ml of acetonitrile, and heated for 4 hours at reflux. After the reaction, the reaction liquid was cooled, and the crystals deposited were filtered off, and recrystallized from a mixed solvent of dimethylformamide and methanol to give Compound (7). Yield 11.2 g and melting point 226°–228° C.

SYNTHESIS EXAMPLE 5

Synthetic method for Illustrative Compound (89)

12.7 g of 2-mercapto-5-phenoxycarbonylamino-1,3,4-thiadiazole was added to 200 ml of acetonitrile, and 6.2 g of 3-N, N-dimethylaminopropylamine was dropwise added thereto at room temperature. After dropping, the reaction liquid was heated with stirring at 50° C. for 1.5 hours, and the crystals deposited were filtered off, and recrystallized from a mixed solvent of methanol and concentrated hydrochloric acid to give Compouhd (89). Yield 10.7 g and melting point 228°–230° C.

SYNTHESIS EXAMPLE 6

Synthetic method for Illustrative Compound (90)

13.3 g of 2-amino-5-mercapto-1,3,4-thiadiazole was dissolved in 100 ml of acetonitrile and 40 ml of dimethylacetamide, and to the resulting solution was added dropwise 15.9 g of 3-(N,N-dimethylamino)propyl isothiocyanate at room temperature. After dropping, the reaction liquid was heated with stirring at 50° C. for 2 hours, and the crystals deposited were filtered off, and recrystallized from a mixed solvent of methanol and concentrated hydrochloric acid to give Compound (90). Yield 12.6 g and melting point 146°–148° C.

SYNTHESIS EXAMPLE 7

Synthetic method for Illustrative Compound (62)

36.6 g of 5-amino-2-mercaptobenzimidazole and 17.1 g of pyridine were added to 250 ml of N,N-dimethylacetamide, and thereto was added dropwise 34.4 g of phenyl chloroformate at room temperature. After the resulting solution as such was stirred for 1.5 hours at room temperature, 1.5 liters of ice cooled water was added to deposit crystals, which were filtered off and recrystallized from acetonitrile, whereby 47.7 g of 2-mercapto-5-phenoxycarbonylaminobenzimidazole was obtained.

To 8.6 g of 2-mercapto-5-phenoxycarbonylaminobenzimidazole thus obtained was added 100 ml of acetonitrile, and heated to 45° C. with stirring, and 14.5 g of N,N-dimethylaminoethylenediamine was added dropwise. The reaction liquid was stirred for 1.5 hours at 45° C., and the crystals deposited were filtered off, and recrystallized from a mixed solvent of N,N-dimethylformamide and methanol, whereby 6.2 g of aimed product was obtained (yield 74%). Melting point 240° C. (decomposed).

SYNTHESIS EXAMPLE 8

Synthetic method for Illustrative Compound (95)

7.8 g of p-(2-N,N-dimethylaminoethoxy)-o-phenylenediamine was added to 120 ml of an ethanolic solution of 2.4 g of potassium hydroxyide, and thereto was added dropwise 12 ml of carbon bisulfide at 40° C. After dropping the reaction liquid was heated for 5 hours at reflux, and after addition of 6 ml of concentrated hydrochloric acid, the solvent was distilled off under diminished pressure. The oily residue thus obtained was purified with silica gel column, and recrystallized from acetonitrile, which gave 3.8 g (yield 40%) of aimed object. Melting point 233°–235° C. (decomposed).

SYNTHESIS EXAMPLE 9

Synthetic method for Illustrative Compound (99)

To 17.2 g of 2-mercapto-6-phenoxycarbonylaminobenzoxazole which was synthesized in the same manner as in SYNTHESIS EXAMPLE 7, was added ethanol, and 6.2 g of N,N-diethylethylenediamine was added dropwise thereto at room temperature. After dropping the reaction liquid was stirred for 30 minutes at 50° C., and then, by cooling to room temperature crystals were deposited. After filtering off the crystals deposited, by recrystallizing from a mixed solvent of N,N-dimethylformamide and acetonitrile, 13.3 g (yield 79%) of aimed product was obtained. Melting point above 280° C. or more (decomposed).

SYNTHESIS EXAMPLE 10

Synthetic method for Illustrative Compound (3)

To 100 ml of ethanol was added first 10.5 g of 2,5-dimercapto-1,3,4-thiadiazole and then, 14 ml of 28% solution of sodium methoxide, and heated to effect dissolution. To the resulting solution was added dorpwise 7.7 ml of 2-methyl-thioethyl chloride and heated for 3 hours at reflux. After the reaction, the reaction liquid was left to cool to room temperature and then poured in 1 liter of ice water. The crystals deposited were filtered off, and recrystallized from a mixed solvent of ethyl acetate and n-hexane, whereby 10.8 g (yield 68.8%) of aimed product was obtained. Melting point 75°–76° C.

SYNTHESIS EXAMPLE 11

Synthetic method for Illustrative Compound (26)

8.6 g of 2-(N-morpholino)ethyl isothiocyanate was added dropwise to a solution containing 7.5 ml of hydrazine hydrate and 30 ml of ethanol under ice cooling, and then stirred for 2 hours. To 9.5 g of the crystals which were obtained by filtering off the precipitate then formed, was added 50 ml of formic acid, and heated for 8 hours at reflux. The reaction liquid was subjected to distillation under diminished pressure, and the residue obtained was neutralized with a 5% aqueous solution of sodium hydroxide, purified with column chromatography (stationary phase, alumina; developing solvent, ethyl acetate/methanol), and further recrystallized from chloroform, whereby 4.9 g of aimed product was obtained. Melting point 146°–147° C.

SYNTHESIS EXAMPLE 12

Synthetic method for Illustrative Compound (28)

To a solution containing 7.5 ml of hydrazine hydrate and 30 ml of ethanol was added slowly 6.5 g of 2-dimethylaminoethyl isothiocyanate under ice cooling, and further stirred for 3 hours. The reaction liquid was added to 100 ml of water, extracted with chloroform, and the organic layer was washed with a saturated aqueous solution of sodium chloride, after which the solvent was distilled off under diminished pressure. To the 7.2 g of the residue obtained was added 36 ml of formic acid, and heated for 8 hours at reflux. The reaction liquid was subjected to distillation under diminished pressure, and the residue obtained was neutralized with a 5% aqueous solution of sodium hydroxide, purified with column chromatography (stationary phase, alumina; developing solvent, ethyl acetate/methanol), and further recrystallized from ethyl acetate/n-hexane, whereby 3.8 g of aimed product was obtained. Melting point 103°–104° C.

SYNTHESIS EXAMPLE 13

Synthetic method for Illustrative Compound (103)

To a solution containing 7.5 ml of hydrazine hydrate and 30 ml of ethanol was added dropwise 7.2 g of 3-dimethylaminopropyl isothiocyanate under ice cooling, and further stirred for 3 hours. The reaction liquid was added to 100 ml of water, extracted with ether, and the ether layer was washed with a saturated aqueous solution of sodium chloride, after which the solvent was distilled off under diminished pressure. To 7.8 g of the residue obtained was added 40 ml of formic acid, and heated for 8 hours at reflux. The reaction liquid was subjected to distillation under diminished pressure, and the residue obtained was neutralized with a 5% aqueous solution of sodium hydroxide, purified with column chromatography (stationary phase, alumina; developing solvent, ethyl acetate/methanol), and further recrystallized from isopropyl alcohol, whereby 4.5 g of aimed product was obtained. Melting point 161°–163° C.

SYNTHESIS EXAMPLE 14

Synthetic method for Illustrative Compound (42)

To a solution of 13.3 g of aminoacetaldehyde diethylacetal in 100 ml of carbon tetrachloride was added slowly 13 g of 2-dimethylaminoethyl isothiocyanate under ice cooling. After stirring for 2 hours at room temperature the solvent was distilled off under diminished pressure. To the residue obtained was added 110 ml of 35% sulfuric acid under ice cooling, and then heated for 3 hours at reflux. The reaction liquid was neutralized with a 30% aqueous solution of sodium hydroxide, and extracted with chloroform. After the organic layer was dried over anhydrous sodium sulfate, the solvent was distilled off under diminished pressure, and the residue obtained was recrystallized from ethyl acetate, whereby 6.8 g of aimed product was obtained. Melting point 130°–131° C.

SYNTHESIS EXAMPLE 15

Synthetic method for Illustrative Compound (43)

To a solution containing 13.3 g of aminoacetaldehyde diethylacetal in 100 ml of carbon tetrachloride was added dropwise 17.2 g of 2-(N-morpholino)ethyl isothiocyanate under ice cooling. After stirring for 2.5 hours at room temperature the solvent was distilled off under diminished pressure. To the residue obtained was added 110 ml of 35% sulfuric acid under ice cooling, and then heated for 4 hours at reflux. The reaction liquid was neutralized with a 30% aqueous solution of sodium hydroxide, and extracted with chloroform. After the organic layer was dried over anhydrous sodium sulfate, the solvent was distilled off under diminished pressure, and the residue obtained was recrystallized from isopropyl alcohol, whereby 7.5 g of aimed product was obtained. Melting point 154°–156° C.

SYNTHESIS EXAMPLE 16

Synthetic method for Illustrative Compound (56)

To a solution obtained by dissolving 7.2 g of sodium azide in 50 ml of water and heating to 80° C. was added dropwise a mixed solution of 17.2 g of 2-(N-morpholino)ethyl isothiocyanate and 20 ml of dioxane, and stirred for 1 hour at 80° C. After the reaction, insoluble matter was filtered away, and 8.8 ml of concentrated hydrochloric acid was added to the filtrate. The crystals deposited were filtered off, and, recrystallized from a mixed solvent of methanol and water, whereby 14.1 g of aimed product was obtained. Melting point 139°–141° C.

SYNTHESIS EXAMPLE 17

Synthetic method for Illustrative Compound (83)

11.2 g of 5-phenoxycarbonylbenzotriazole and 4.4 g of N,N-dimethylethylenediamine were added to 150 ml of benzene and heated for 4 hours at reflux. After cooling the reaction liquid to room temperature, the crystals deposited were filtered off, and recrystallized from methanol, whereby 7.9 g of aimed product was obtained. Melting point 182°–184° C.

Nucleation promoters may be incorporated either in the photosensitive material or in the processing solution, but they should preferably be incorporated in the photosensitive material, above all, in the emulsion of silver halide of internal latent image type or other hydrophilic colloid layers (interlayer or protective layer, etc.). More preferably they are incorporated in the emulsion of silver halide or in the adjacent layers thereof.

The amount of nucleation promoters to be added is preferably from $10^{-6}$ to $10^{-2}$ mol, or more preferably from $10^{-5}$ to $10^{-2}$ mol, per mol of silver halide.

Further, when nucleation promoters are added to the processing solution, i.e., the developing solution or pretreatment bath therefor it is preferably from $10^{-8}$ to $10^{-3}$ mol, or more preferably from $10^{-7}$ to $10^{-4}$ mol, per liter.

The emulsions of silver halide of internal latent image type used in this invention, which have not been preliminarily fogged, are the emulsions containing silver halide such that the surfaces of the silver halide grains are not preliminarily fogged, and moreover, the latent image is mainly formed in the interior of the grains. More specifically, they may be defined as follows; that is, in the case where a definite amount of silver halide emulsion is coated on a transparent support and after an exposure to light for a fixed period of time from 0.01 to 10 seconds and the subsequent development processing, the maximum density is measured by the conventional method of photographic density measurement, the maximum density obtained when the developing solution used is a developing solution A as shown below (a developing solution of internal type) and the development is carried out for 5 minutes at 18° C., should be preferably at least 5 times or more preferably at least 10 times large as compared with the maximum density obtained when the developing solution used is a developing solution B as also shown below (a developing solution of surface type) and the development is carried out for 6 minutes at 20° C.

| Internal developing solution A | |
|---|---|
| Metol | 2 g |
| Sodium sulfite (anhydrous) | 90 g |
| Hydroquinone | 8 g |
| Sodium carbonate (monohydrate) | 52.5 g |
| KBr | 5 g |
| KI | 0.5 g |
| Water to make | 1 liter |
| Surface developing solution B | |
| Metol | 2.5 g |
| l-ascorbic acid | 10 g |
| $NaBO_2.4H_2O$ | 35 g |
| KBr | 1 g |
| Water to make | 1 liter |

Specific examples of emulsions of internal latent image type include the emulsions of silver halide of conversion type described in the specification of U.S. Pat. No. 2,592,250; the emulsions of silver halide of core/shell type as disclosed in U.S. Pat. Nos. 3,761,276, 3,850,637, 3,923,513, 4,035,185, 4,395,478, 4,504,570, Japanese Patent Applications (OPI) Nos. 156614/77, 127549/80, 60222/78, 22681/81, 208540/84, 107641/85, 3137/86, Japanese Patent Application No. 3642/86, Research Disclosure 23510 (November, 1983) p. 236, etc.

The shape of the grains of the silver halide used in this invention may be in a regular crystal form, such as a cube, an octahedron, a dodecahedron, a tetradecahedrons, etc.; an irregular form, such as a sphere; a form of tabular grains having an aspect ratio of 5 or more, or a composite form of various crystal forms. Also, grains having different forms may be in admixture.

As the composition of the silver halide there may be mentioned silver chloride, silver bromide; and silver mixed halide, of which the preferable in this invention are silver chloro (iodo)bromide, silver (iodo) chloride, or silver (iodo) bromide which contain no silver iodide or contain not more than 3% of silver iodide.

The average grain size of the silver halide is preferably not more than 2 microns and not less than 0.1 micron, and more preferably not more than 1 micron and not less than 0.15 micron. The grain size distribution may be narrow or broad, but in order to improve granularity and sharpness, it is preferable in this invention to employ the so-called "monodisperse" silver halide emulsion which has a narrow size distribution such that more than 90% of all the grains have the grain size within the range of ±40%, or preferable ±20% of the number averaged or weight averaged grain size. Further, in order to satisfy the gradation aimed by the photosensitive material in an emulsion layer having a substantially the same color sensitivity, two or more monodisperse silver halide emulsions having different grain sizes, or a plurality of grains having the same size but different sensitivities may be mixed in the same layer or separately coated on different layers which are later placed one over another. Still further, two or more kinds of polydisperse silver halide emulsions or combinations of monodisperse emulsion and polydisperse emulsion may be used in admixture or in layers placed one over another.

The silver halide emulsions used in this invention can be chemically sensitized by subjecting the interior or the surface of the silver halide grains to sulfur or selenium sensitization, reduction sensitization, noble metal sensitization, etc., singly or in combination. More specific examples of these sensitizations are described in Research Disclosure 17643-III (December, 1978) p-23, etc.

The photographic emulsions used in this invention can be spectrally sensitized by photographic sensitizing dyes in a routine manner. Especially useful dyes are those belonging to cyanine dyes, merocyanine dyes, and complex merocyanine dyes, and these dyes may be used singly or in combination. The above-described dyes may also be used in combination with supersensitizers. More specific examples are described in Research Disclosure 17643-IV (December, 1978) p. 23–24, etc.

The photographic emulsions used in this invention can contain a fog inhibitor or a stabilizer for the purpose of either preventing fogging during the manufacturing step, during the storage, or during the photographic processing of the photosensitive material, or stabilizing the photographic performance of the photographic material. More specific examples are described, for instance, in Research Disclosure 17643-IV (December, 1978), E. J. Birr: "Stabilization of Photographic Silver Halide Emulsions" (Focal Press), 1974, etc.

For the purpose of forming a direct positive color image use can be made of various color couplers. Useful preferable couplers are compounds capable of forming or releasing a dye upon the coupling reaction with the oxidation product of an aromatic primary amine series developing agent, and they are themselves preferably substantially nondiffusible compounds. Typical examples of such useful color couplers include naphthol or phenol series compounds, pyrazolohe or pyrazoloazole series compounds and open-chained or heterocyclic ketomethylene compounds. Specific examples of these cyan-, magenta-, and yellow-color couplers usable in this invention are described in Research Disclosure 17643 (December, 1978) p. 25, VII -D, ibid. 18717 (November, 1979), Japanese Patent Application No. 32462/86, and patents cited therein.

Above all, as the typical examples of the yellow couplers usable in this invention there may be mentioned yellow two-equivalent couplers of oxygen atom cleaving type or nitrogen atom cleaving type. Especially preferable are α-pivaloylacetanilide series couplers which are excellent in the fastness, especially in the lightfastness of the color developed dyes and α-benzoylacetanilide series couplers which can give a high coloring density.

Also, the 5-pyrazolone series magenta couplers preferably used in this invention are 5-pyrazolone series couplers whose 3-position is substituted by an arylamino group or an acylamino group (above all, two-equivalent couplers of sulfur atom cleaving type).

More preferable couplers are pyrazoloazole series couplers, and above all the pyrazolo[5,1-c][1,2,4]triazoles described in U.S. Pat. No. 3,725,067 are desirable, the imidazo-[1,2-b]pyrazoles described in U.S. Pat. No. 4,500,630 is more desirable in the point that the color developed dyes have light fastness showing little yellow side-absorption, and the pyrazolo[1,5-b][1,2,4]triazole described in U.S. Pat. No. 4,540,654 is still further desirable.

The cyan couplers preferably used in this invention are naphthol and phenol series couplers described in U.S. Pat. Nos. 2,474,293, 4,052,212, etc. and phenol series cyan couplers having an alkyl group such as ethyl or higher at the m-position of the phenol nucleus described in U.S. Pat. No. 3,772,002. Besides the above, 2,5-diacylamino substituted phenol series couplers are also preferable in the point of color image fastness.

Preferabel yellow couplers are illustrated below.

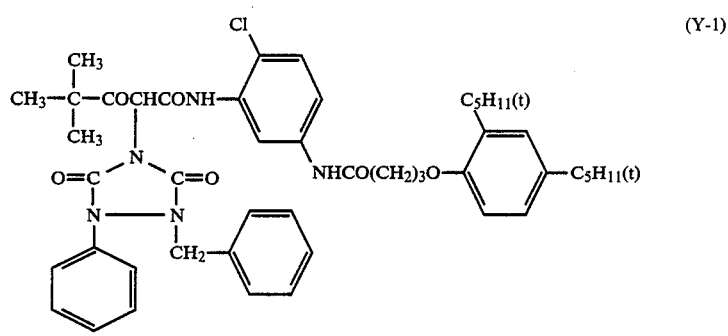
(Y-1)

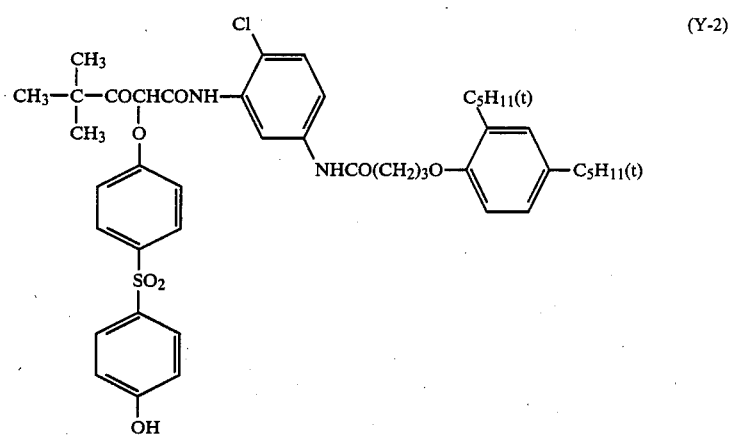
(Y-2)

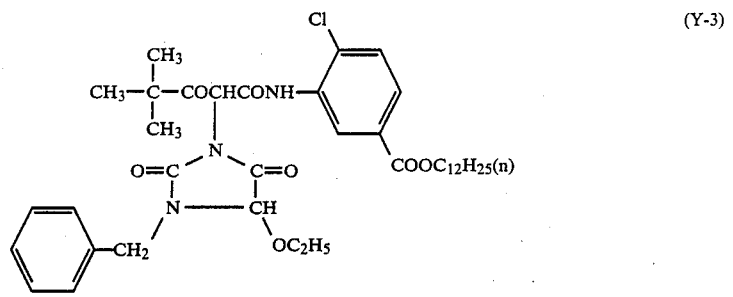
(Y-3)

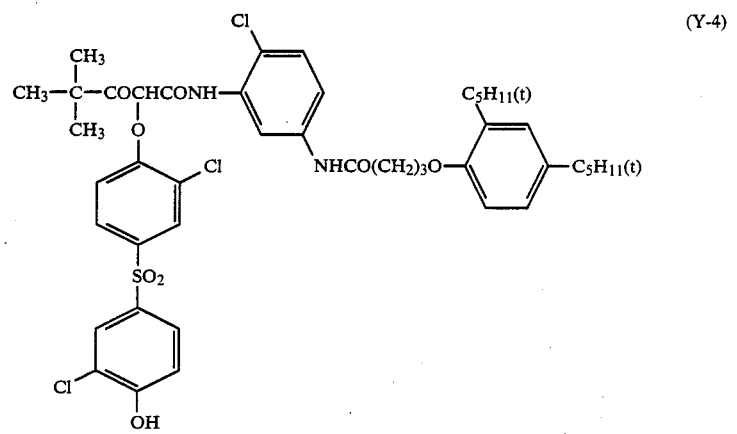
(Y-4)

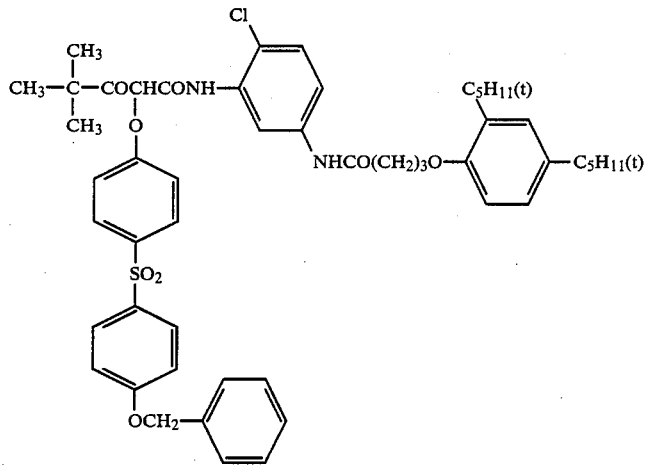
(Y-5)
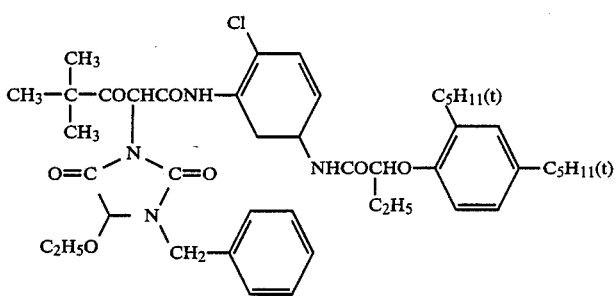
(Y-6)
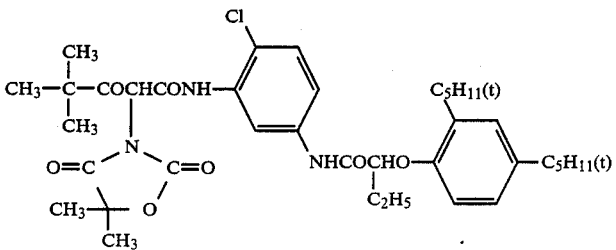
(Y-7)
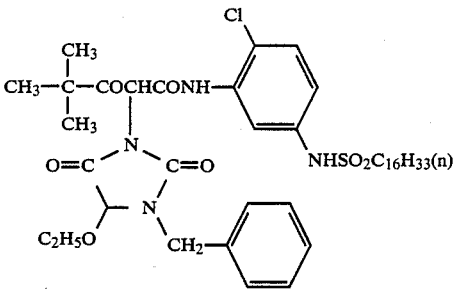
(Y-8)
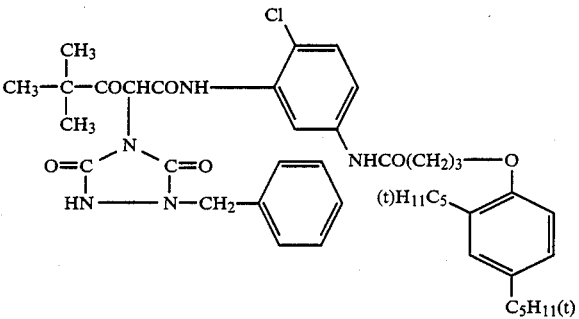
(Y-9)

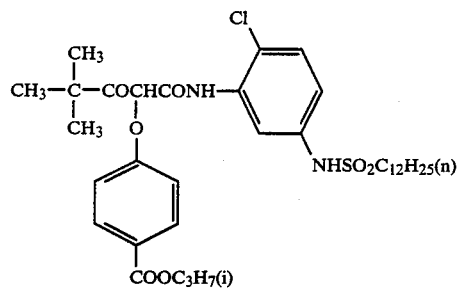
(Y-10)
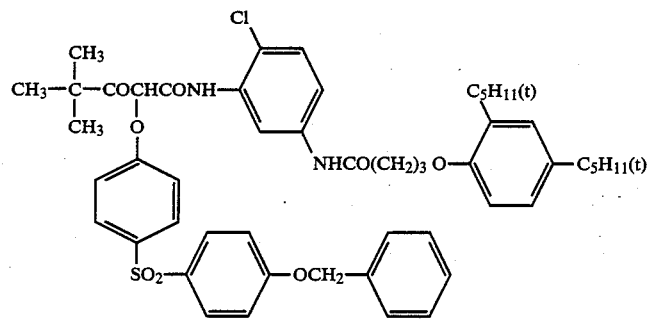
(Y-11)
Preferable magneta couplers are illustrated below.
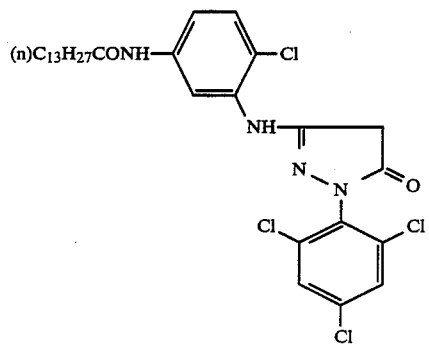
(M-1)
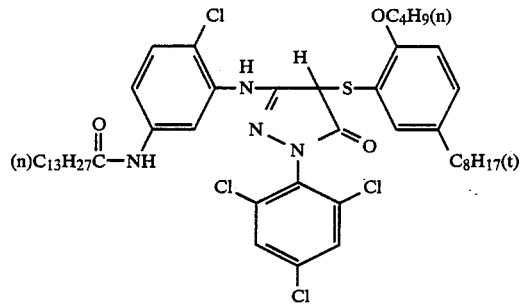
(M-2)
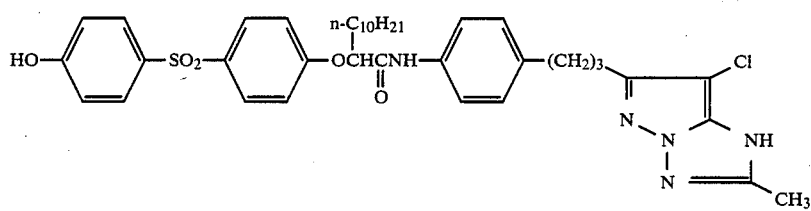
(M-3)

(M-4)
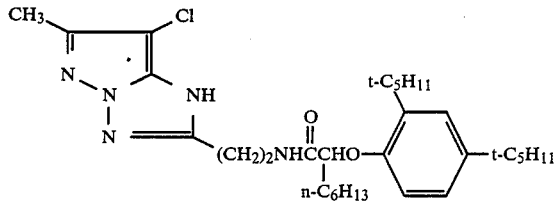
(M-5)
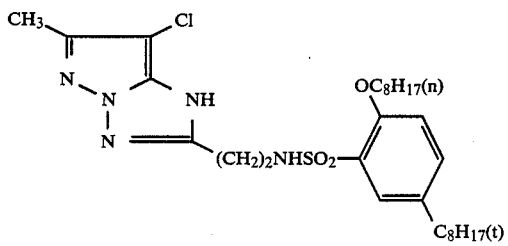
(M-6)
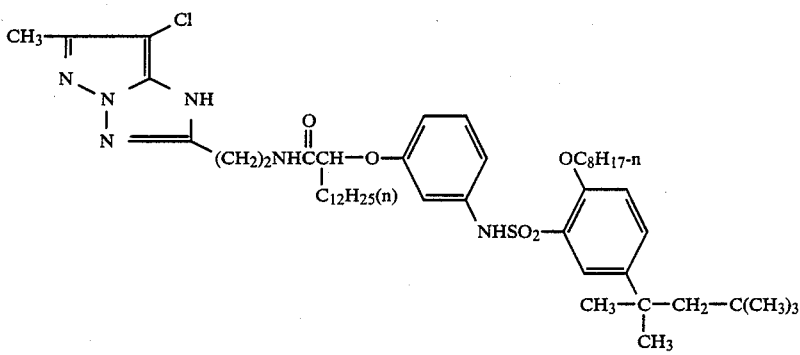
(M-7)
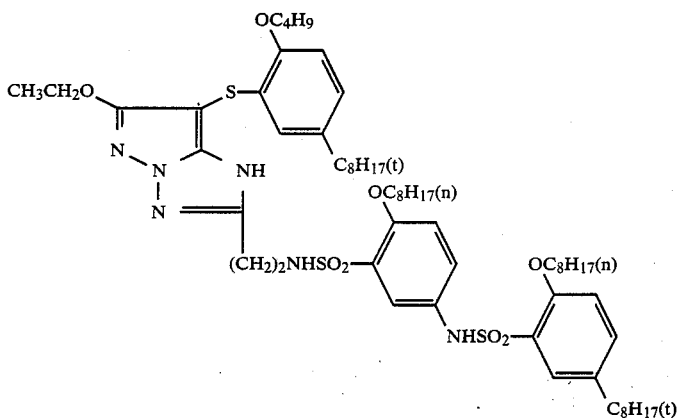
(M-8)
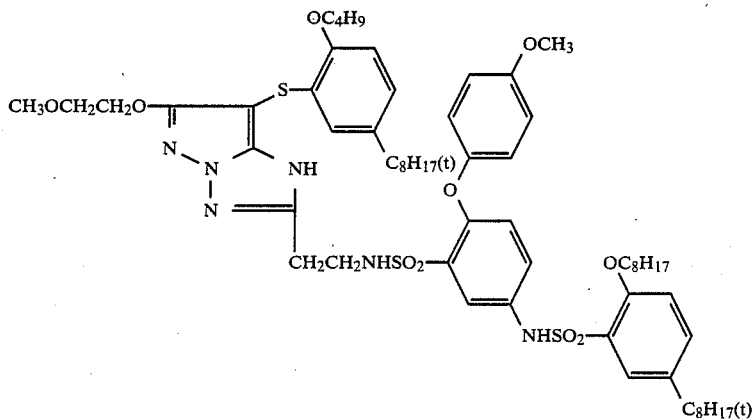

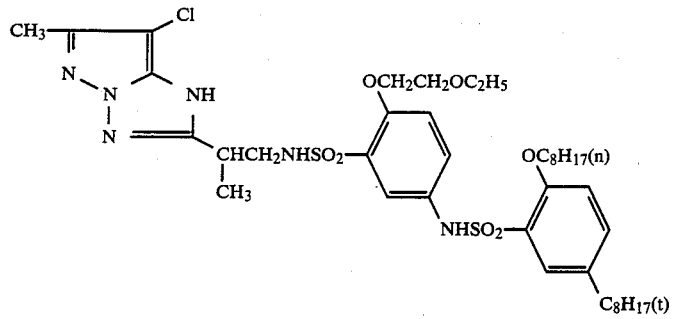
(M-9)
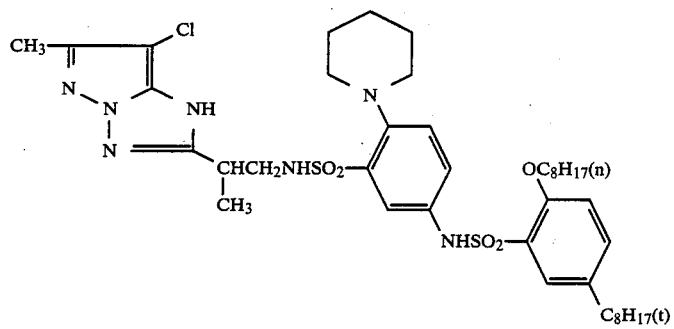
(M-10)
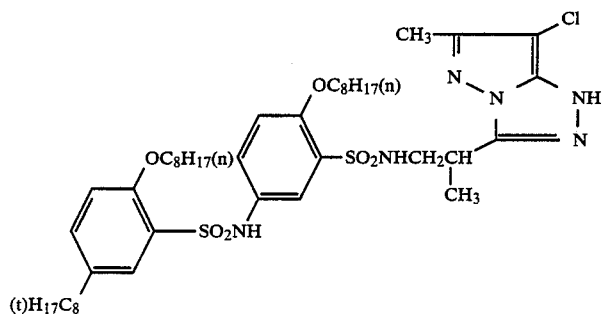
(M-11)
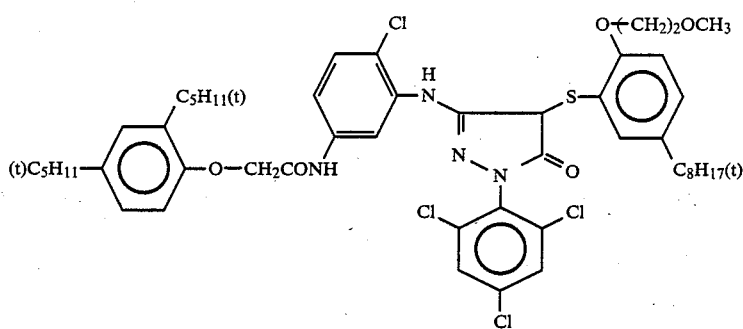
M-12
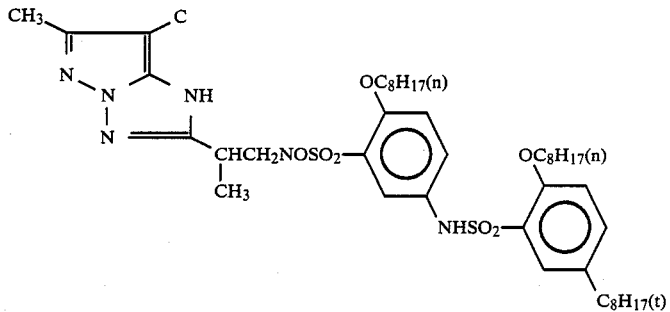
M-13

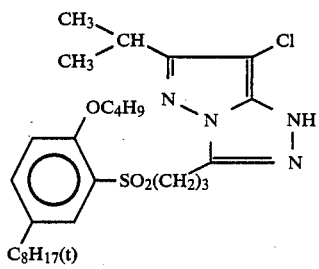
M-14
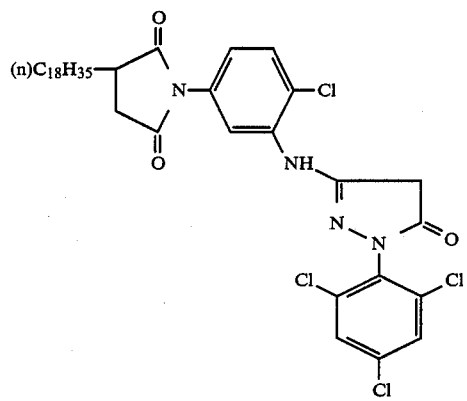
M-15
Preferable cyan couplers are illustrated below.
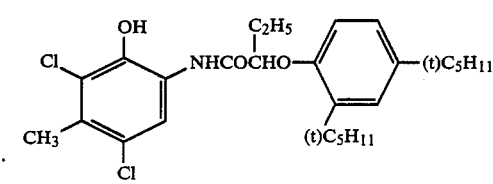
(C-1)
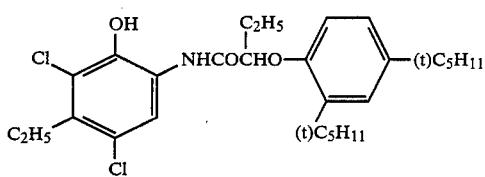
(C-2)
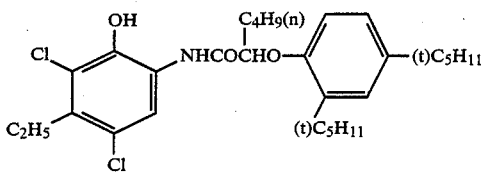
(C-3)
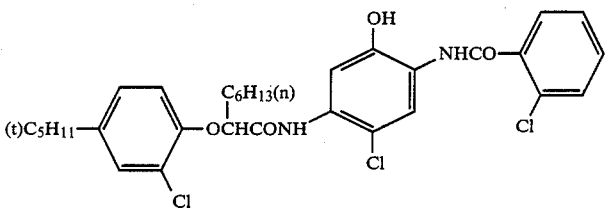
(C-4)

-continued

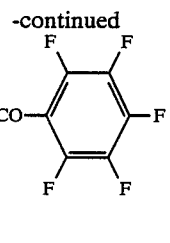
(C-5)

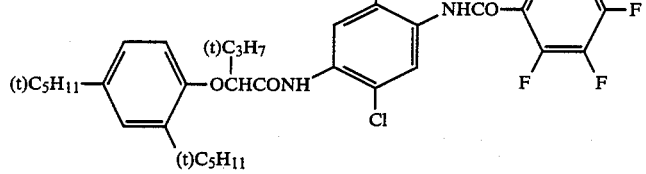

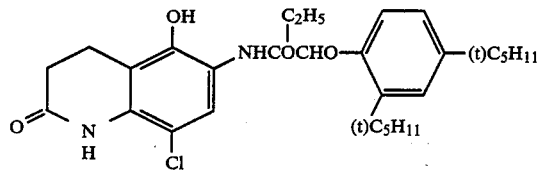
(C-6)

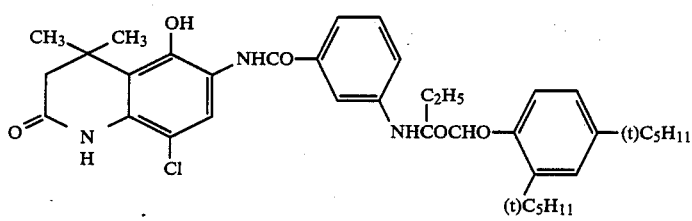
(C-7)

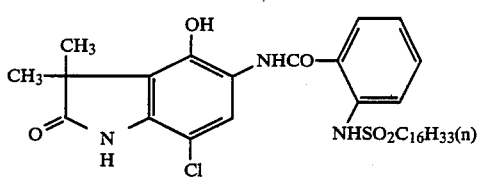
(C-8)

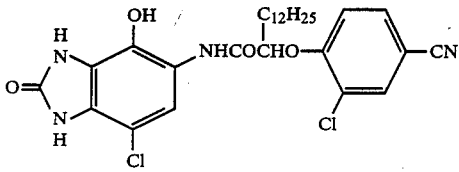
(C-9)

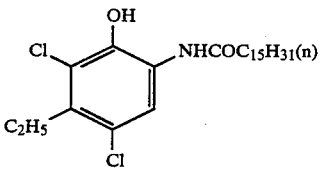
(C-10)

(C-11)

In order to correct the unnecessary absorption which the dye formed has in the short wavelength region, use can also be made of colored couplers, couplers which can produce a dye having moderate diffusibility, non-coloring couplers, DIR couplers or couplers capable of releasing a development accelerator upon the coupling reaction, or polymerized couplers.

The standard amount of the color couplers used is in the range of from 0.001 to 1 mol per mol of sensitized silver halide, and preferably from 0.01 to 0.5 mol for yellow coupler, from 0.003 to 0.5 mol for magenta coupler, and from 0.002 to 0.5 mol for cyan coupler.

In this invention supersensitizers may also be used for the purpose of improving the color developing property of couplers. Typical examples of these compounds are described in Japanese Patent Application No. 32462/86, pp. 374–391.

Couplers of this invention are dissolved in a high boiling organic solvent and/or a low boiling organic solvent, and emulsified into an aqueous solution of gelatin or other hydrophilic colloids by the high speed stirring in a homogenizer, etc., by the mechanical fine division in a colloid mill etc., or by the technical means utilizing supersonic waves, and then added to an emulsion layer. In the above case a high boiling organic solvent need not always be used, but the use of compounds described in Japanese Patent Application No. 32462/86 pp. 440–467 is preferable.

Couplers of this invention can be dispersed in hydrophilic colloids by the method described in Japanese Patent Application No. 32462/86, pp. 468–475.

The photosensitive materials prepared in accordance with this invention can contain a color fog inhibitor or a compound color inhibitor such as hydroquinone derivatives, aminophenol derivatives, amines, gallic acid derivatives, catechol derivatives, ascorbic acid derivatives, non-coloring couplers, sulfonanidophenol derivatives, etc.

Typical examples of color fog inhibitors and compound color inhibitors are described in Japanese Patent Application No. 32462/86, pp. 600–630.

In the photosensitive materials of this invention various discoloration inhibitors can be used. Typical examples of organic discoloration inhibitors include hydroquinones, 6-hydrocoumarone, 5-hydroxycoumarans, spirocoumarones, p-alkoxyphenols, hindered phenols centering about bisphenols, gallic acid derivatives, methylenedioxybenzenes, aminophenols, hindered amines, and ether or ester derivatives obtained by silylating or alkylating the phenolic hydroxyl group of these compounds. Also, metal complexes as typified by (bis-salicylaldoximato)-nichel complex and (bis-N,N-dialkyldithiocarbamato) nickel complex can be used.

The compounds containing structures of both hindered amine and hindered phenol moieties in the same molecule as described in U.S. Pat. No. 4,268,593 have favarable effects upon the prevention of deterioration of yellow dye images due to heat, moisture, and light. Also, in order to prevent the deterioration of magenta dye image especially due to light, spiroindans described in Japanese Patent Application (OPI) No. 159644/81 and hydroquinone diether or monoether substituted coumarones described in Japanese Patent Application (OPI) No. 89835/80 have desirable effects.

Typical examples of these discoloration inhibitors are described in Japanese Patent Application No. 32462/86 pp. 401–440.

To achieve the object of these compounds, they are usually co-emulsified with couplers in a proportion of from 5 to 100 wt % on the basis of the weight of the corresponding color couplers. In order to prevent the deterioration of cyan dye images due to heat and especially light, it is effective to introduce ultraviolet absorbents into the layers on both sides adjacent to the cyan color developing layer. Further, ultraviolet absorbents can also be added to hydrophilic colloid layers as protective layers or the like. Typical examples of such compounds are described in Japanese Patent Application No. 32462/86, pp. 391–400.

As the binder or the protective colloid which can be used in the emulsion layers or interlayers of the photosensitive materials of this invention gelatin can be used to advantage, but the other hydrophilic colloids can also be used.

Dyes preventing irradiation or halation, ultraviolet absorbents, plasticizers, fluorescent whitening agents, matting agents, air fog inhibitors, coating aids, film hardeners, antistatic agents, slide improving agents, etc. can be added to the photosensitive materials of this invention. Typical examples of these additives are described in Research Disclosure 17643 VII–VIII (December, 1978) pp. 25–27 and ibid. 18716 (November, 1979) pp. 647–651.

This invention can also be applied to a multilayer multicolor photosensitive material having at two different spectral sensitivities on a support. A multilayer natural color photographic material has, in general, at least one each red-sensitive emulsion layer, green-sensitive emulsion layer, and blue-sensitive emulsion layer on a support. The order of these layers can be chosen as desired. The preferable order of arrangement of emulsion layers is red-sensitive, green-sensitive, and blue-sensitive from the side of the support, or green-sensitive, red-sensitive, and blue-sensitive from the side of the support. Each of the above-described emulsion layers may be made of two or more emulsion layers having different sensitivities, or a nonphotosensitive layer may be present between two or more emulsion layers having the same sensitivity. Usually, cyan-forming couplers are incorporated in red-sensitive emulsion layers, magenta-forming couplers, in green-sensitive emulsion layers, and yellow-forming couplers, in blue-sensitive emulsion layers, respectively, but different combinations may also be taken as occasion demands.

In the photosensitive materials of this invention, it is preferred that auxiliary layers are suitably provided such as protective layers, interlayers, filter layers, halation inhibiting layers, back layers, white reflecting layers, etc.

In the photosensitive materials of this invention, the photographic emulsions and other layers are coated on the supports described in Research Disclosure 17643 XVII (December, 1978), p.28 and the supports described in European Pat. No. 182,253 and Japanese Patent Application (OPI) No. 97655/86. Also, the method of coating described in Research Disclosure 17643 XV, pp. 28–29 is applicable to this invention.

This invention is applicable to various color photosensitive materials.

For instance, the typical examples include color reversal films, color reversal papers, etc. for slide use or television use. This invention can also be applied to color hard copies, etc. for preserving the images by full color duplicating machine or CRT. This invention can further be applied to black-and-white photosensitive materials utilizing the three color coupler process described in Research Disclosure 17123 (July, 1978), etc.

The fogging treatment used in the process for direct formation of a positive color image in this invention may be carried out either by fogged exposure, so-called a "light fogging method" or in the presence of a nucleating agent, so-called a "chemical fogging method". A photosensitive material containing a nucleating agent may also be subjected to fogged exposure.

The overall exposure, i.e., fogged exposure in this invention is carried out prior to the development processing and/or during the development processing after an exposure to light through a pattern. The photosensitive materials exposed to light through a pattern are exposed to light while they are immersed in the developing solution or in the pretreatment bath, or they are not as yet dried after having been taken out from these solutions. However, it is most preferable that they are exposed to light in the developing solution.

As the light source for the fogged exposure any of the light sources emitting the light within the range of the sensitive wavelengths of the photosensitive materials may be used. In general, a fluorescent lamp, a tungsten lamp, a xenon lamp, the sun light, etc. can be used. Details concerning these methods are described, for instance, in British Pat. No. 1,151,363, Japanese Patent Publication Nos. 12710/70, 12709/70, 6936/83, Japanese Patent Applications (OPI) Nos. 9727/73, 137350/81, 129438/82, 62652/83, 60739/83, 70223/83 (corresponding to U.S. Pat. No. 4,440,851), 120248/83 (corresponding to U.S. Pat. No. 89101A2) etc. For the photosensitive materials having sensitivity over the whole wavelength region, for instance, such as a color photosensitive material, highly color rendering light sources (close to white as much as possible) as described in Japanese Patent Application (OPI) Nos. 137350/81 or 70223/83 are preferable. The luminous intensity of the light is from 0.01 to 2000 luxes, preferably from 0.05 to 30 luxes, or more preferably from 0.05 to 5 luxes. The higher the sensitivity of the emulsion used in a photosensitive material, the more preferable a low-intensity exposure. For the adjustment of illumination intensity the brightness of the light source may be varried or reduced by various filters, or the distance or angle between the photosensitive material and the light source may be altered. It is also possible to use a feeble light in the early stage of exposure and then to use a stronger light for the purpose of shortening the time of exposure.

It is preferable that light is irradiated after the photosensitive material has been immersed in the developing solution or in the pretreatment bath until the solution sufficiently penetrates into the emulsion layer of the photosensitive material. The time interval of from the immersion of the photosensitive material in the developing solution until it is subjected to fogged exposure is usually from 2 seconds to 2 minutes, preferably from 5 seconds to 1 minute, or more preferably from 10 seconds to 30 seconds.

The time of exposure for fogging is usually from 0.01 second to 2 minutes, preferably from 0.1 second to 1 minute, or more preferably from 1 second to 40 seconds.

In this invention nucleating agents can be used in combination with nucleation promoters.

As the nucleating agents usable in this invention all the compounds which have hitherto been developed for the purpose of nucleating the silver halide of internal latent image type are applicable. Specific examples of these nucleating agents include the compounds described in the specification pp. 49–66 of Japanese Patent Application (2) filed on Oct. 27th, 1986 (Applicant: Fuji Photo Film Co., Ltd.), and more specifically Examples (N-I-1)–(N-I-10) described in ibid. pp. 56–58, Examples (N-II-1)–(N-II-12) described in ibid. pp. 63–66, etc. Also, the amount of the nucleating agents used and the place of addition of the nucleating agents are described in ibid. pp. 66–67.

Two or more kinds of nucleating agents may be used in combination.

To explain more fully with regard to nucleating agents, many compounds of this sort which can be divided into three groups of quarternary heterocyclic compounds (represented by general formula [N-I]), hydrazine series compounds (represented by general formula [N-II]), and other compounds, are disclosed in Research Disclosure, No. 22534 (January, 1983) pp. 50–54, ibid. No. 15162(November, 1976) pp. 76–77, and ibid. No. 23510(November, 1983), pp. 346–352.

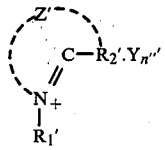

General Formula [N-I]

(In the above formula, $Z'$ represents a substituted unsubstituted nonmetallic atomic group required for the formation of 5- to 6-membered heterocyclic ring;. $R_1'$ is an aliphatic group, and $R_2'$ is a hydrogen atom, an aliphatic group, or an aromatic group $R_1'$ and $R_2'$ may be a substituted or unsubstituted group, but, of the groups represented by $R_1'$, $R_2'$, and $Z'$ at least one contains an alkynyl group, an acyl group, a hydrazine group, or a hydrazone group, or $R_1'$ and $R_2'$ form a 6-membered ring having the skeleton of dihydropyridinium. Moreover, of the substituent groups of $R_1'$, $R_2'$, and $Z'$ at least one may have $X_1'(L^1)_{\overline{m''}}$, wherein $X_1'$ is an adsorption promoting group to silver halide, and $L^1$ is a divalent connecting group. $Y'$ is a counter ion for the charge balance, $n''$ is 0 or 1, and $m''$ is 0 or 1.)

Specific examples of the heterocyclic rings completed by $z'$ include quinolinium, benzothiazolium, benzimidazolium, pyridinium, thiazolium, naphthothiazolium, thiazolium, selenazolium, benzoselenazolium, imidazolium, tetrazolium, indolenium, pyrrolinium, acridinium, phenanthridinium, isoquinolinium, oxazolium, naphthooxazolium, and benzoxazolium nuclei. As the substituent groups to $Z'$ there may be mentioned an alkyl group, an alkenyl group, an aralkyl group, an aryl group, an alkynyl group, a hydroxyl group, an alkoxy group, an aryloxy group, a halogen atom, an amino group, an alkylthio group, an arylthio group, an acyloxy group, an acylamino group, a sulfonyl group, a sulfonyloxy group, a sulfonylamino group, a carboxyl group, an acyl group, a carbamoyl group, a sulfamoyl group, a sulfo group, a cyano group, a ureido group, a carbonic acid ester group, a hydrazine group, a hydrazone group, an imino group, etc. As the substituent group to $Z'$, of the above-described substituent groups at least one can be chosen, and when two or more of them are chosen they may be the same or different. Also, the above described substituent groups may be further substituted with these substituent groups.

Further, the substituent groups to $Z'$ may form a heterocyclic quaternary ammonium group which is completed by $Z'$ through the medium of suitable connecting group L, in which case the so-called dimer structure results.

The heterocyclic rings completed by $Z'$ are preferably quinolinium, benzothiazolium, benzimidazolium, pyridinium, acridinium, phenanthridinium, and isoquinolinium nuclei. The more preferable are quinolinium, benzothiazolium, and the most preferable is quinolinium.

The aliphatic groups represented by $R_1'$ and $R_2'$ are substituted or unsubstituted alkyl groups containing from 1 to 18 carbon atoms. As the substituent groups there may be mentioned those which have been described with respect to the substituent groups to $Z'$.

The aromatic groups represented by $R_2'$ are those which contain from 6 to 20 carbon atoms, such as, for example, a phenyl group, a naphthyl group, etc. As the substituent groups there may be mentioned those which have been described with respect to the substituent groups to Z'. R$_2$' is preferably an aliphatic group, and most preferably a methyl group and a substituted methyl group.

Of the groups represented by R$_1$', R$_2$, and Z' at least one has an alkynyl group, an acyl group, a hydrazine group, or a hydrazone group, or R$_1$' and R$_2$' form a 6-membered ring having the skeleton of dihydropyridinium, but these may be substituted with the groups earlier described as the substituent groups to Z'.

At least one of the substituent groups to the groups or rings represented by R$_1$', R$_2$', and Z' is preferably an alkynyl group or an acyl group, or R$_1$' and R$_2$' are preferably connected with each other to form the skeleton of dihydropyridinium. The case where at least one alkynyl groups is contained is most preferable.

The preferable examples of the adsorption promoting groups to silver halide which are represented by X$_1$' are a thioamido group, a mercapto group, or a 5- to 6-membered nitrogen-containing heterocyclic group.

These groups may be substituted with the groups earlier described as the substituent groups to Z'. Preferable thioamido groups are acyclic thioamido groups (e.g., thiourethane, thioureido, etc.).

As the mercaptogroups of X$_1$' heterocyclic mercapto groups (e.g., 5-mercaptotetrazole, 3-mercapto-1,2,4-triazole, 2-mercapto-1,3,4-thiadiazole, etc.) are especially preferable.

The 5- to 6-membered nitrogen-containing heterocyclic rings represented by X$_1$' consist of a combination of nitrogen, oxygen, sulfur, and carbon, and the preferable is one producing imine silver, for example, benzotriazole.

The divalent connecting group represented by L$^1$ is an atom or an atomic group containing at least one of C, N, S, and O. Specially, such a connecting group is individually an alkylene group, an alkenylene group, an alkynylene group, an arylene group, —O—, —S—, —NH—, —N—, —CO—, —SO$_2$—, etc. (these groups may have a substituent group), or combinations thereof.

As the counter ion Y' for the charge balance, there are, for example, bromine ion, chlorine ion, iodine ion, p-toluenesulfonate ion, ethylsulfonate ion, perchlorate ion, trifluoromethane sulfonate ion, thiocyanate ion, etc.

Examples and processes for synthesis of these compounds are described, for instance, in the patents cited in Research Disclosure No. 22534 (January, 1983) pp. 50—54 and No. 23213 (August, 1983) pp. 267–270, Japanese Patent Publications Nos. 38164/74, 19452/77, 47326/77, Japanese Patent Applications (OPI) Nos. 69613/77, 3426/77, 138742/80, 11837/85, U.S. Pat. Nos. 4,306,016, and 4,471,044.

Specifical examples of the compounds represented by the general formula [N-I] are shown below, but this invention should not be construed as being limited thereto.

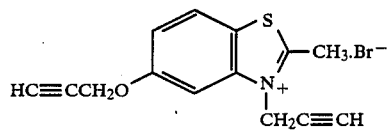

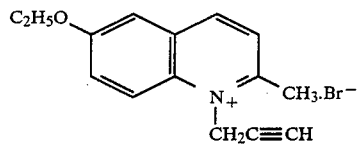

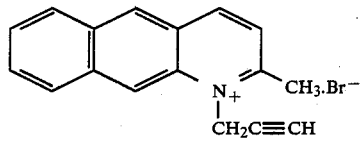

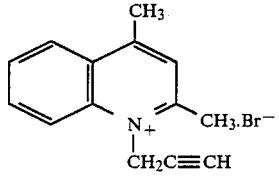

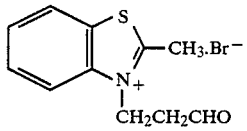

-continued
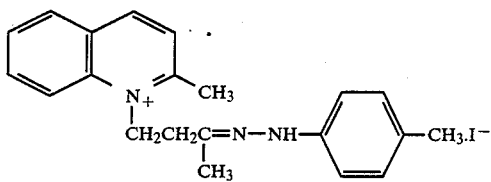 (N-I-6)
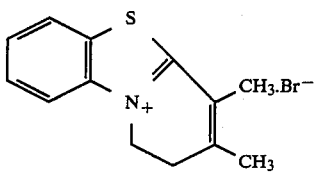 (N-I-7)
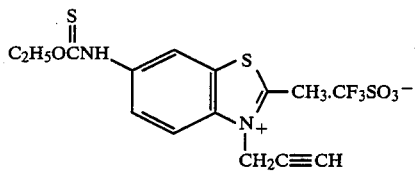 (N-I-8)
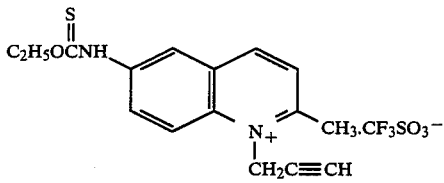 (N-I-9)
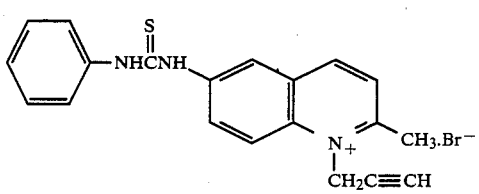 (N-I-10)
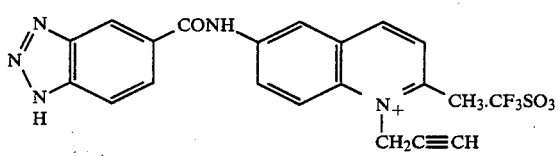 (N-I-11)
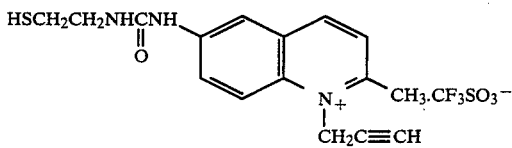 (N-I-12)
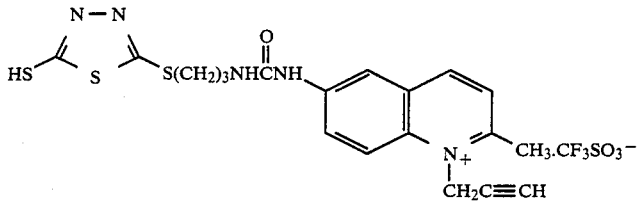 (N-I-13)

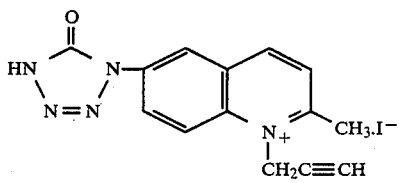

(N-I-14)

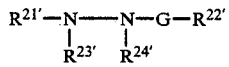

(In the above formula, $R_{21}'$ represents an aliphatic group, an aromatic group, or a heterocyclic group; $R_{22}'$ represents a hydrogen atom, an alkyl group, an aralkyl group, an aryl group, an alkoxy group, an aryloxy group, or an amino group; G represents a carbonyl group, a sulfonyl group, a sulfoxy group, a phosphoryl group, or animinomethylene group (HN=C<); and $R_{23}'$ and $R_{24}'$ represent a hydrogen atom, or either of them represents a hydrogen atom while the other represents any one of an alkylsulfonyl group, an arylsulfonyl group, or an acyl group. Also, G, $R_{23}'$, $R_{24}'$, and hydrazine nitrogen may form a structure of hydrazone (>N—N=C<) in the form taken together. Further, the above-described groups may be substituted with a substituent group if possible.)

To explain more fully, $R_{21}'$ may be substituted by the following substituent groups, which may be further substituted. For examples, an alkyl group, an aralkyl group, an alkoxy group, an aryl group, a substituted amino group, an acylamino group, a sulfonylamino group, a ureido group, a urethane group an aryloxy group, a sulfamoyl group, a carbamoyl group, an aryl group, an alkylthio group, an arylthio group, a sulfonyl group, a sulfinyl group, a hydroxyl group, a halogen atom, a cyano group, a sulfo group, a carboxyl group, etc. Of these a ureido group is especially preferable.

These groups may also be connected with each other to form a ring.

The preferable as $R_{21}'$ are an aromatic group, an aromatic heterocyclic ring, or an aryl substituted methyl group, and more preferable are aryl groups such as, for example, phenyl, naphthyl, etc.

The preferable of the groups represented by $R_{22}'$ are a hydrogen atom, an alkyl group (e.g., methyl), or an aralkyl group (e.g., o-hydroxybenzyl, etc.), etc. and a hydrogen atom is especially preferable.

As the substituent groups to $R_{22}'$ those which have been enumerated with respect to $R_{21}'$ are applicable, and in addition to them, for example, an acyl group, an acyloxy group, an alkyl or aryloxycarbonyl group, an alkenyl group, an alkynyl group, a nitro group, etc. are also applicable.

These substituent groups may further be substituted with these substituent groups. Also, if possible they may be connected with each other to form a ring.

$R_{22}'$, above all $R_{21}'$ may contain a nondiffusible group, or so-called ballast group, such as a coupler (especially preferable in the case where connection is made with a ureido group).

They may also contain a group $X_2'(L^2)_{m2}$ which can promote the adsorption on the surface of silver halide grains. In the above formula, $X_2'$ has the same meaning as $X_1'$ in the general formula [N-I], and it is preferably a thioamido group (except thiocarbazide and derivatives thereof), an mercapto group, or a 5- to 6-mem- bered nitrogen-containing heterocyclic group. $L^2$ represents a divalent connecting group, having the same meaning as $L^1$ in the general formula [N-I], $m_2$ is 0 or 1.

The preferable $X_2'$ are an acyclic thioamido group (e.g., thioureido, thiourethane, etc.), a cyclic thioamido group (i.e., mercapto substituted nitrogen-containing heterocyclic rings such as, for example, 2-mercaptothiadiazole, 3-mercapto-1,2,4-triazole, 5-mercaptotetrazole, 2-mercapto-1,3,4-oxadiazole, 2-mercaptobenzoxazole, etc.), or nitrogen-containing heterocyclic group (e.g., benzotriazole, benzimidazole, indazole, etc.).

The most preferable $X_2'$ may be mentioned to differ depending on the photosensitive material. For instance, when in color photosensitive materials use is made of a color material which forms a dye upon the coupling reaction with an oxidation product of a p-phenylenediamine series developing agent (so-called a coupler), a mercapto substituted nitrogen-containing heterocyclic ring or a nitrogen-containing heterocyclic rin which can form iminosilver is preferable as $X_2'$. On the other hand, when in color photosensitive materials use is made of a color material which forms a diffusible dye by crossoxidizing an oxidation product of a developing agent (so-called a DRR compound), an acyclic thioamido group or a mercaptosubstituted nitrogen-containing heterocyclic ring is preferable as $X_2'$.

Further, in black-and-white photosensitive materials a mercapto substituted nitrogen-containing heterocyclic ring or a nitrogen-containing heterocyclic ring which can form iminosilver is preferable as $X_2'$.

As $R_{23}'$ and $R_{24}'$ a hydrogen atom is most preferable.

As G in the general formula [N-II] a carbonyl group is most preferable.

And as the general formula [N-II] those which have a group being adsorbed on silver halide or a ureido group are preferable.

As for the examples and the processes for synthesis of these compounds, firstly the examples of the hyrazine series nucleating agents having a group being adsorbed on silver halide are described, for instance, in U.S. Pat. Nos. 4,030,925, 4,080,207, 4,031,127, 3,718,470, 4,269,929, 4,276,364, 4,278,748, 4,385,108, 4,459,347, 4,478,928, 4,560,638, British Pat. No. 2,011,391B, Japanese Patent Applications (OPI) Nos. 74729/79, 163533/80, 74536/80, 179734/85, etc.

Examples of the other hydrazine series nucleating agents are described, for instance, in Japanese Patent Application (OPI) No. 86829/82, U.S. Pat. Nos. 4,560,638, 4,478,928, 2,563,785, and 2,588,982.

Specific examples of the compounds represented by the general formula [N-II] are shown below. But this invention should not be construed as being limited thereto.

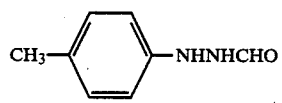 (N-II-1)
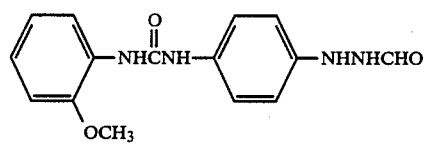 (N-II-2)
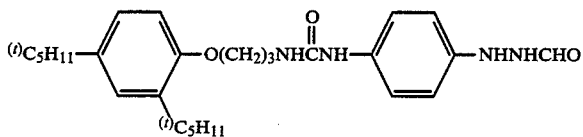 (N-II-3)
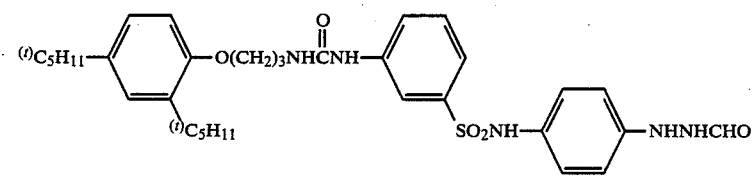 (N-II-4)
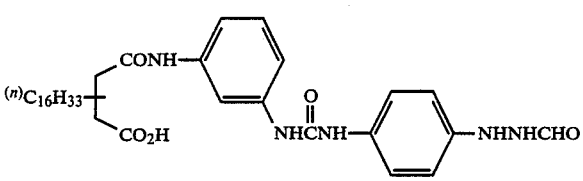 (N-II-5)
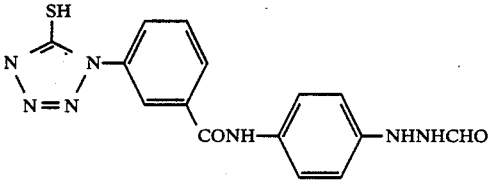 (N-II-6)
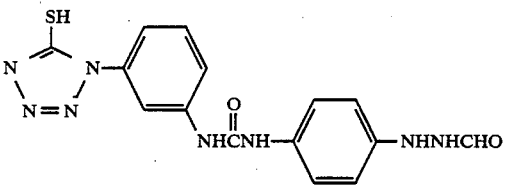 (N-II-7)
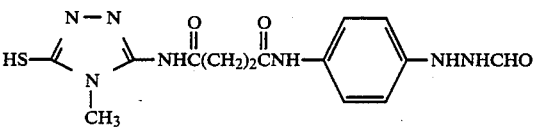 (N-II-8)
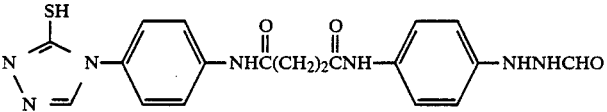 (N-II-9)
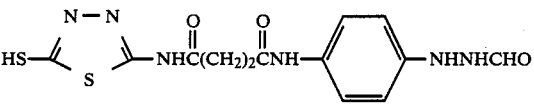 (N-II-10)

-continued
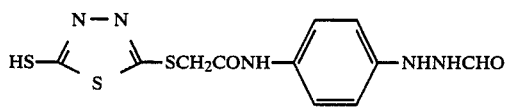 (N-II-11)
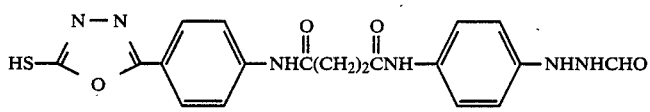 (N-II-12)
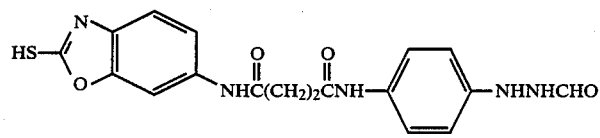 (N-II-13)
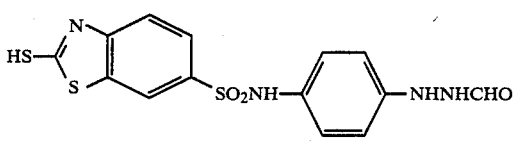 (N-II-14)
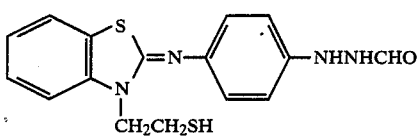 (N-II-15)
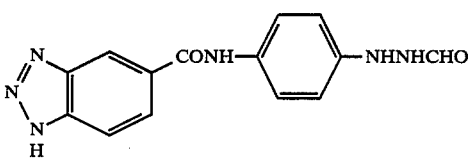 (N-II-16)
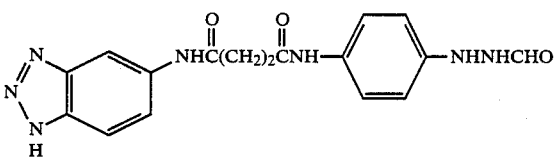 (N-II-17)
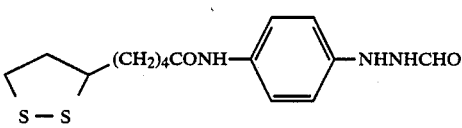 (N-II-18)
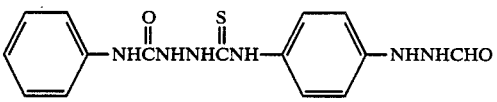 (N-II-19)
 (N-II-20)
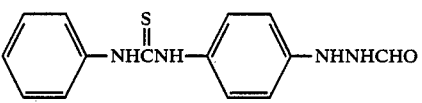 (N-II-21)

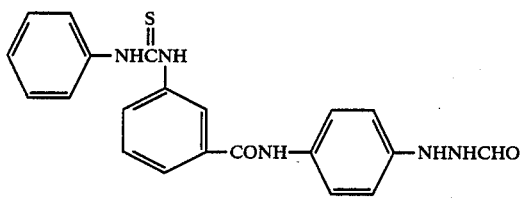
(N-II-22)

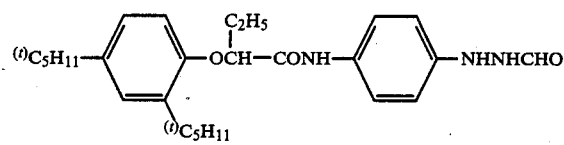
(N-II-23)

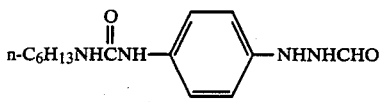
(N-II-24)

The nucleating agents used in this invention can be incorporated in the photosensitive materials or in the processing solution of the photosensitive materials. They may preferably be incorporated in the photosensitive materials.

In the case where they are incorporated in the photosensitive materials, their addition to the emulsion layer of silver halide of the internal latent image type is preferable, but, so long as the nucleating agents can be adsorbed on silver halide through the diffusion during the coating or processing, they may be added to the other layers such as the interlayers, subbing layers, or backing layers. In the case where they are added to the processing solution they may be added to the developing solution or to the pretreatment bath at a low pH as described in Japanese Patent Application (OPI) No. 178350/83.

When nucleating agents are incorporated in the photosensitive materials, the amount thereof used is preferably from $10^{-8}$ to $10^{-2}$ mol, or more preferably from $10^{-7}$ to $10^{-3}$ mol per mol of silver halide.

Also, when nucleating agents are added to the processing solution, the amount thereof used is preferably from $10^{-5}$ to $10^{-1}$ mol, or more preferably from $10^{-4}$ to $10^{-2}$ mol per liter.

For the purposes of increasing the maximum image density, lowering the minimum image density, improving the storage stability of the photosensitive materials, or accelerating the speed of development the following compounds may be added.

Hydroquinones (e.g., compounds described in U.S. Pat. Nos. 3,227,552 and 4,279,987), coumarones (e.g., compounds described in U.S. Pat. No. 4,268,621, Japanese Patent Application (OPI) No. 103031/79, Research Disclosure No. 18264 (June, 1979) pp. 333-334), quinones (e.g., compounds described in Research Disclosure No. 21206 (December, 1981) pp. 433-434), amines (e.g., compounds described in U.S. Pat. No. 4,150,993, Japanese Patent Application (OPI) No. 174757/83), oxidizing agents (e.g., compounds described in Japanese Patent Application (OPI) No. 260039/85, Research Disclosure No. 16936 (May, 1978) pp. 10-11), catechols (e.g., compounds described in Japanese Patent Applications (OPI) No. 21013/80 and 65944/80), compounds capable of releasing a nucleating compound at the time of development (e.g., compounds described in Japanese Patent Application (OPI) No. 107029/85), thioureas (e.g., compounds described in Japanese Patent Application (OPI) No. 95533/85), and spirobisindans (e.g., compounds described in Japanese Patent Application (OPI) No. 65944/80).

The color developing solution used in the development processing of the photosensitive materials in this invention contains substantially no solvent of silver halide, and is preferably an alkaline aqueous solution consisting mainly of an aromatic primary amine series color developing agent. The pH of the color developing solution is not higher than 11.5, preferably not lower than 9.5, and more preferably from 11.2 to 9.8.

Further, the color developing solution in this invention contains substantially no benzyl alcohol. When a replenishment color developing solution of low replenishment type is prepared, benzyl alcohol is contained therein, it happens sometimes that either the dissolution takes much time on account of its slow rate of dissolution, or tarry matter is formed. Whereas, a color developing solution containing no benzyl alcohol indicates that the time of dissolution is short, and no tarry matter is formed even if it is of low replenishment type, so that it has an advantage in that the replenishment developing solution of low replenishment type can be readily prepared.

The color developer which is used for developing color photographic materials in this invention is an alkaline aqueous solution containing substantially no silver halide solvent and preferably containing an aromatic primary amino color developing agent as the main component. As the color developing agent, an aminophenol compound can be used, but a p-phenylene diamine compound is preferably used. Typical examples of such a p-phenylene diamine compound include 3-methyl-4-amino-N,N-diethylaniline, 3-methyl-4-amino-N-ethyl-N-B-hydroxyethylaniline, 3-methyl-4-amino-N-ethyl-N-B-methylsulfonamidoethylaniline, 3-methyl-4-amino-N-ethyl-N-B-methoxyethylaniline, and sulfates, hydrochlorides, phosphates, p-toluenesulfonates, tetraphenylborates, and p-(t-octyl)benzenesulfonates thereof. These diamines are generally stable in the salt form rather than in the free state.

The present color developing agent is generally used in the concentration of from about 0.1 g to about 30 g, preferably about 1 g to about 15 g per 1 of color developing solution. The amount of the present color developing solution to be refilled can be reduced by using a refilling solution whose concentration of silver halide, color developing agent, or the like has been properly adjusted.

The present color development time is normally 5 minutes or less. In order to speed processing, color development time is preferably 2 minutes and 30 seconds or less, more preferably from 10 seconds to 2 minutes. If a sufficient color density can be obtained, a shorter color development time is preferably use. The pH thereof is not higher than 11.5, preferably from 9.5-11.2, and more preferably 10.0-11.0.

The color developer in this invention contains substantially no benzyl alcohol. If a color developer contains benzyl alcohol, it takes a long time to prepare the replenisher for the low-replenishing type color developer due to the low dissolution rate of benzyl alcohol and also tarry materials sometimes form. On the other hand, a color developer containing no benzyl alcohol has the advantage that the replenisher for the low-replenishing type color developer can be easily prepared since the time required for dissolving components is short, even when the color developer is of a low-replenishing type, and tarry materials do not form.

Also, by preventing the deviation of liquid composition or performing continuous processing using a color developer containing no benzyl alcohol, a constant finish without deviations in the degree of color stain is obtained without the formation of tarry materials, even when the amount of the replenisher is reduced to less than half (less than 165 ml/m$^2$) of the standard replenisher rate.

As additives for the color developer in this invention, various compounds described in Japanese Patent Application (OPI) Nos. 144739/85, pp. 14–22, 242161/85, pp. 45–50. Furthermore, it is particularly preferred to use nitrogen-containing heterocyclic compounds (e.g., tetraazaindenes, benzindazoles, benzotriazoles, benzimidazoles, benzothiazoles, benzoxazoles, 1-phenyl-5-mercaptotetrazoles, etc.), and aromatic or aliphatic mercapto compounds for the color developers in this invention as antifoggant.

The present color developing solution may contain a pH buffer and a metallic chelate preservative compound as described in Japanese Patent Application No. 23462/86. The present color developing solution may also contain halide ion such as a bromide ion and an iodide ion, and a competing coupler such as citrazinic acid.

The photographic emulsion layer which has been color-developed is generally subjected to bleaching. Bleaching may be carried out in a combined bleach and fixing (blix) at the same time with fixing or separate from the fixing step. In order to further speed processing, the photographic emulsion layer which has been bleached may be subjected to blix or the photographic emulsion layer which has been fixed may be subjected to blix.

As a bleaching agent for bleach or blix there may preferably be used an organic complex salt or persulfate or iron (III) to attain faster processing and prevent pollution.

Examples of organic complex salts iron (III) which preferably be used because of its high belaching power include iron (III) complex salts of ethylenediaminetetraacetic acid, diethylenetriaminepentaacetic acid, cyclohexanediaminetetraacetic acid, 1,2-diaminopropanetetraacetic acid, methyliminodiacetic acid, 1,3-diaminopropanetetraacetic acid, and glycoletherdiaminetetraacetic acid.

Examples of persulfates which may preferably be used in the present invention include persulfates of alkali metals such as potassium persulfate and sodium persulfate, and ammonium persulfate.

The amount of the bleaching agent in 1 l of the bleaching solution is preferably in the range of from 0.1 to 2 mol. A suitable pH range for the bleaching solution is from 0.5 to 8.0 if a ferric ion complex salt is used, particularly from 4.0 to 7.0 if a ferric ion complex salt of aminocarboxylic acid, aminopolyphosphonic acid, phosphonocarboxylic acid, or organic phosphonic acid is used. If a persulfate is used, the concentration of the solution is from 0.1 to 2 mol/l and its pH value is preferably in the range of from 1 to 5.

As a suitable fixing agent for fixing or blix, any suitable known fixing agent may be used. Examples of such fixing agents include thiosulfates such as sodium thiosulfate and ammonium thiosulfate, thiocyanates such as sodium thiocyanate and ammonium thiocyanate, thioether compounds such as ethylenebisthioglycolic acid, and 3,6-dithia-1,8-octanediol, and water-soluble silver halide solvent such as thiourea. These compounds may be used singly or in admixture.

With regard to fixing or blix, the concentration of the fixing agent is preferably from 0.2 to 4 mol/l. In blix, the concentration of ferric ion complex salt and fixing agent are preferable from 0.1 to 2 mol and from 0.2 to 4 mol per 1 l of blix solution, respectively. The pH value of the fixing solution or blix solution is preferably in the range of from 4.0 to 9.0, particularly from 5.0 to 8.0.

Besides the above additives, the present fixing solution or blix solution may contain as a preservative a sulfite such as sodium sulfite, potassium sulfite, and ammonium sulfite, bisulfite, hydroxylamine, hydrazine, or bisulfite addition product of aldehyde compound such as sodium acetaldehyde bisulfite. The present fixing solution or blix solution may further contain various fluorescent brightening agents, antifoaming agents, surface active agents, and organic solvents such as polyvinyl pyrrolidone, and methanol.

When the color developer does not contain benzyl alcohol, a leuco-forming reaction of cyan dye is not as likely to occur in a blix liquid, so that the pH of the blix liquid or the amount of an oxidant in the blix liquid can be reduced.

The amount of the replenisher for a blix liquid containing benzyl alcohol is usually from about 330 ml/m$^2$, but when a color developer does not contain benzyl alcohol, the amount of the replenisher can be reduced to below 60 ml/m$^2$.

The bleaching solution, blix solution and their prebaths may optionally comprise any suitable bleach accelerators. Specific examples of such useful bleach accelerators include compounds containing mercapto or disulfide groups, thiazolidine derivatives, thiourea derivatives, iodides, polyethyleneoxides, polyamines, compounds as described in Japanese Patent Application (OPI) Nos. 42434/74, 59644/74, 94927/78, 35727/79, 26506/80, and 163940/83, iodine ion, and bromine ion. Among these compounds, the compounds containing mercapto or dilsulfide groups are preferably used in light of its excellent effect of accelerating bleaching. In particular, compounds as described in U.S. Pat. No. 3,893,858, West German Pat. No. 1,290,812, and Japanese Patent Application (OPI) No. 95630/78 are preferably used. Furthermore, compounds as described in U.S. Pat. No. 4,552,834 are preferably used. These bleach accelerators may be incorporated in the light-sensitive material.

The fixing or blix process is generally followed by a processing step such as rinsing and stabilization.

In order to prevent precipitation or improve the stability of rinsing water, various known compounds may be incorporated in the rinsing and stabilizing process. Examples of such known compounds which may be optionally incorporated in these processing steps include chelating agents such as inorganic phosphoric acid, aminopolycarboxylic acid, and organic phosphonic acid, germicides or anti-fungal agents for inhibiting generation of various bacteria, molds or fungi such as compounds described in *Journal of Antibacterial and Antifungal Agents* (Vol. 11, No. 5, pp. 207 to 223, 1983) and compounds as described in *BOKIN BOBAI NO KAGAKU* (Antibacterial and antifungal chemistry) (edited by Hiroshi Horiguchi), metal salts such as aluminum salts, and ammonium salts, and surface active agents for preventing drying load and mark. Furthermore, compounds as described in *Photographic Science and Engineering* (Vol. 6, pp. 344 to 359, 1965) may be used. In particular, chelating agents, germicides or antifugal agents may be effectively used. The rinsing process is generally multistage counterflow using two or more tanks (e.g., 2 to 9 tanks) to same rinsing water. The rinsing process can be replaced by a multistage counterflow stabilizing process as described in Japanese Patent Application (OPI) No. 8543/82. In order to stabilize image, the present stabilizing bath may comprise various compounds besides the above mentioned additives. Typical examples of such compounds include various buffers for adjusting the pH of the film (at e.g., 3 to 9) such as borate, metaborate, borax, phosphate, carbonate, potassium hydroxide, sodium hydroxide, ammonia water, monocarboxylic acid, dicarboxylic acid, polycarboxylic acid, combinations thereof, and aldehydes such as formalin. Other examples of such compounds include chelating agents such as inorganic phosphoric acid, aminocarboxylic acid, organic phosphonic acid, aminopolyphosphonic acid, and phosphonocarboxylic acid, germicides, antifungal agents such as a thiazole, isothiazole, halogenated phenol, sulfanylamide, and benzotriazole, surface active agents, fluorescent brightening agents, metal salts of film hardeners, and other various additives. Two or more compounds for the same or different purposes may be based in combination.

Various ammonium salts such as ammonium chloride, ammonium nitrate, ammonium sulfate, smmonium phosphate, ammonium sulfite, and ammonium thiosulfate may be preferably used as a pH adjustor for film which has been processed in order to improve image stability.

The present rinsing or stabilizing time depends on the type and processing conditions of the light-sensitive material to be processed. It is generally in the range of from 20 seconds to 10 minutes, preferably from 20 seconds to 5 minutes.

These various processing solutions of the present invention may be used at a temperature of from 10° to 50° C. The standard temperature is in the range of from 33° to 38° C. However, a higher temperature range can be used to accelerate processing so that processing time can be shortened. On the contrary, a lower temperature range can be used to improve picture quality of the stability of the processing solution.

For a continuous processing step, fluctuation in solution composition can be prevented by using replenisher for each processing solution so that a constant finish can be provided.

The amount of replenisher to be used for each processing step is preferably as small as possible. The preferably 3 to 30 times the amount of solution brought from prebath per unit area of light-sensitive material.

Each processing bath may optionally be provided with a heater, temperature sensor, liquid level sensor, circulating pump, filter, floating cover, and squeegee.

In order to simplify the speed processing, the present silver halide color light-sensitive material may comprise a color developing agent or precursor thereof. To this end, a precursor of a color developing agent is preferably used because it provides better stability for the light-sensitive material. Specific examples of such a color developing agent precursor include indoaniline compounds, Schiff base type compounds, aldol compounds, and urethane compounds.

In order to accelerate color development, the present silver halide color photographic material may contain various 1-phenyl-3-pyrazolidones.

The amount of replenishment of the bleaching-fixing solution is usually about 330 ml/m$^2$, and in the case where benzyl alcohol is absent in the color developing solution, it is possible to reduce the amount of replenishment to less than 60 ml/m$^2$.

After the desilvering (blix or fixing) processings such as water wash and/or stabilization are carried out. As the additives used in the water wash and stabilization steps, various compopunds described in Japanese Patent Application No. 32462/86 specification pages 30 to 36.

The amount of replenishment in each processing step should preferably be small. The amount of replenishment is preferably from 0.1 to 50 times, or more preferably from to 30 times, the amount carried into from the preceding bath per unit area of the photosensitive material.

EXAMPLE 1

Formulation of Emulsion A

By adding simultaneously an aqueous solution of potassium bromide and an aqueous solution of silver nitrate to an aqueous solution of gelatin to which had been added 3,4-dimethyl-1,3-thiazoline-2-thione in an amount of 0.3 g per mol of Ag with vigorous stirring at 75° C. over about 20 minutes, there was obtained an octahedron monodisperse silver bromide emulsion having an average grain size of 0.4 micron. By adding to this emulsion 6 mg each per mol of Ag of sodium thiosulfate and chloroauric acid (tetrahydrate) and heating at 75° C. for 80 minutes chemical sensitization was carried out. The silver bromide grains thus obtained were further allowed to grow with these grains being dealt with as the cores by treating them for 40 minutes in the same precipitation environment as the first treatment, whereby there was obtained finally an octahedron monodisperse core/shell silver bromide emulsion having an average grain size of 0.7 micron. After water wash and desalting, to this emulsion were added 1.5 mg each per mol of Ag of sodium thiosulfate and chloroauric acid (tetrahydrate) and heated at 60° C. for 60 minutes to effect the chemical sensitization, which gave Emulsion A of silver halide of internal latent image type. The coefficient of variation of the grain size was 10%.

Using the above-described internal latent imaged Emulsion A of core/shell type, wholly laminated color printing paper composed of the layers as shown in Table 1 was prepared on a paper support laminated with polyethylene on both sides. The coating solution was prepared as follows.

Preparation of the first layer coating solution:

To 10 g of cyan coupler (a) and 2.3 g of color image stabilizer (b) were added 10 ml of ethyl acetate and 4 ml of solvent (c) to give a solution, which was allowed to disperse as emulsion in 90 ml of 10% aqueous solution of gelatin containing 5 ml of 10% sodium dodecylbenzenesulfonate. On the other hand, by adding a red-sensitive dye as described below to the above-described was prepared 90 g of red-sensitive emulsion. The emulsified dispersion, emulsion, and development accelerator (d) were dissolved by mixing, and then the concentration was adjusted using gelatin so as to obtain the composition as shown in Table 1, and further, by adding thereto the nucleation promoters as shown in Table 3, there was prepared the coating solution for the first layer.

The coating solutions for the second to seventh layers were also prepared in the same manner as the first layer coating solution. As the gelatin hardener in each layer sodium salt of 1-oxy-3,5-dichloro-s-triazine was used.

As the spectral sensitizer of each emulsion the following were used.

| Layer | Main composition | | Amount used |
|---|---|---|---|
| The seventh layer (Protective layer) | Latex particles of polymethyl methacrylate (average grain diameter 2.8 microns) | | 0.05 g/m$^2$ |
| | Gelatin | | 1.33 g/m$^2$ |
| | Acryl modified copolymer of polyvinyl alcohol (degree of modification 1 7%) | | 0.17 g/m$^2$ |
| The sixth layer (Ultraviolet absorptive layer) | Gelatin | | 0.54 g/m$^2$ |
| | Ultraviolet absorbent | (i) | 5.10 × 10$^{-4}$ mol/m$^2$ |
| | Solvent | (k) | 0.08 g/m$^2$ |
| The fifth layer (Blue-sensitive layer) | Emulsion A | | 0.40 g/m$^2$ |
| | Gelatin | | 1.35 g/m$^2$ |
| | Yellow coupler | (l) | 6.91 × 10$^{-4}$ mol/m$^2$ |
| | Color image stabilizer | (m) | 0.13 g/m$^2$ |
| | Solvent | (h) | 0.02 g/m$^2$ |
| | Development accelerator | (d) | 32 mg/m$^2$ |
| The fourth layer (Ultraviolet absorptive layer) | Gelatin | | 1.60 g/m$^2$ |
| | Colloidal silver | | 0.10 g/m$^2$ |
| | Ultraviolet absorbent | (i) | 1.70 × 10$^{-4}$ mol/m$^2$ |
| | Compound color inhibitor | (j) | 1.60 × 10$^{-4}$ mol/m$^2$ |
| | Solvent | (k) | 0.24 g/m$^2$ |
| The third layer (Green-sensitive layer) | Emulsion A | | 0.18 g/m$^2$ |
| | Gelatin | | 1.56 g/m$^2$ |
| | Magenta coupler | (f) | 4.60 × 10$^{-4}$ mol/m$^2$ |
| | Color image stabilizer | (g) | 0.14 g/m$^2$ |
| | Solvent | (h) | 0.42 g/m$^2$ |
| | Development accelerator | (d) | 32 mg/m$^2$ |
| The second layer (Compound color inhibitor) | Gelatin | | 0.90 g/m$^2$ |
| | Colloidal silver | | 0.02 g/m$^2$ |
| | Compound color inhibitor | (e) | 2.33 × 10$^{-4}$ mol/m$^2$ |
| The first layer (Red-sensitive layer) | Emulsion A | | 0.39 g/m$^2$ |
| | Gelatin | | 0.90 g/m$^2$ |
| | Cyan coupler | (a) | 7.05 × 10$^{-4}$ mol/m$^2$ |
| | Color image stabilizer | (b) | 5.20 × 10$^{-4}$ mol/m$^2$ |
| | Solvent | (c) | 0.22 g/m$^2$ |
| | Development accelerator | (d) | 32 mg/m$^2$ |
| Support | Polyethylene laminated paper (white pigment (TiO$_2$, etc.) and bluish dye (ultramarine, etc.) are contained in polyethylene on the side of the first layer) | | Thickness: 135 microns |
| Curl preventive layer | Gelatin | | 5.0 g/m$^2$ |
| Protective layer | Same as the seventh layer | | Same as the seventh layer | silver halide emulsion (containing Ag 70 g/kg) in an amount of 2.0×10$^{-4}$ mol per mol of silver halide there As the irradiation preventive dyes the following dyes were used.

Irradiation preventing dye for
green-sensitive emulsion layer

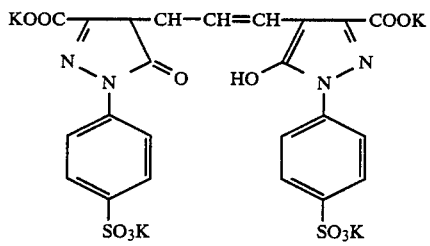

Irradiation preventing dye for
red-sensitive emulsion layer

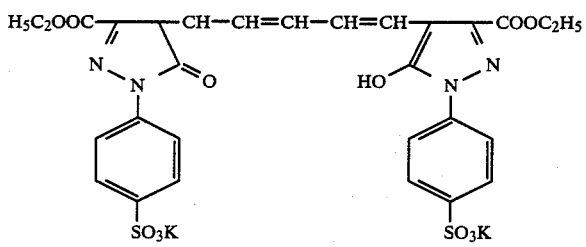

Spectral sensitizing dyes

Red-sensitive emulation layer:

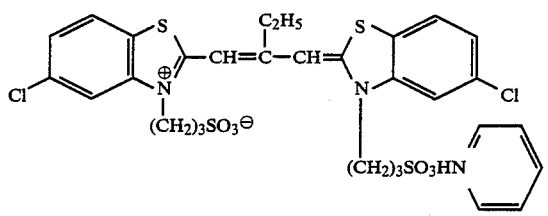

Green-sensitive emulsion layer:

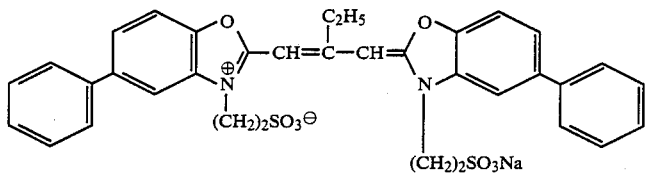

Blue-sensitive emulsion layer:

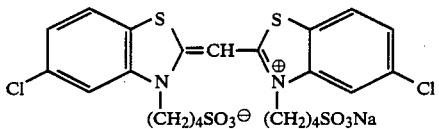

The structural formulae of the compounds such as couplers used in the invention are shown below.

(a) Cyan Coupler 1:1 Mixture (mol ratio) of (C-2) and (C-4)

(b) Color image stabilizer 1:3:3 Mixture (mol ratio) of

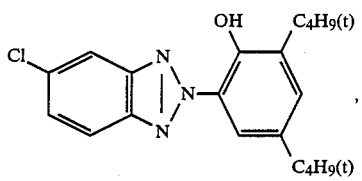

,

-continued

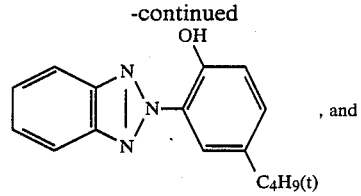

, and

-continued

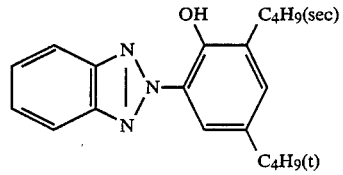

(c) Solvent

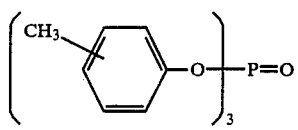

(d) Development accelerator

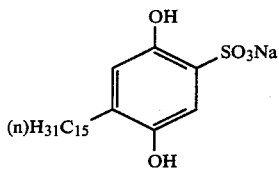

(e) Color mixing inhibitor

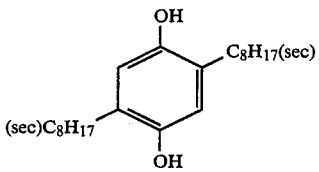

(f) Magenta coupler (M-13)

(g) Color image stabilizer

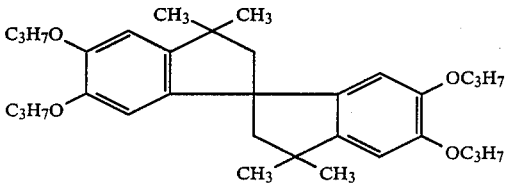

(h) Solvent: 2:1 Mixture (weight ratio) of

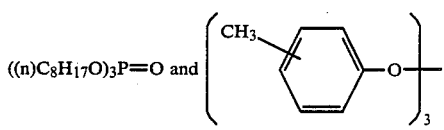

(i) Ultraviolet absorbent: 1:5:3 Mixture of

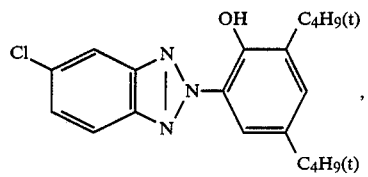

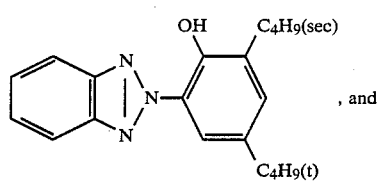

, and

-continued

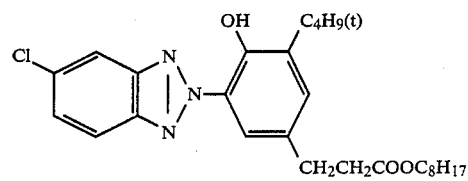

(j) Color mixing inhibitor

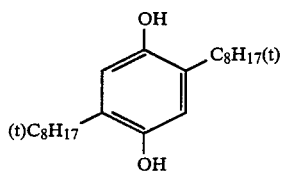

(k) Solvent

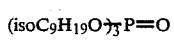

$(isoC_9H_{19}O)_3P=O$ (l) Yellow coupler (Y-6)

(m) Color image stabilizer

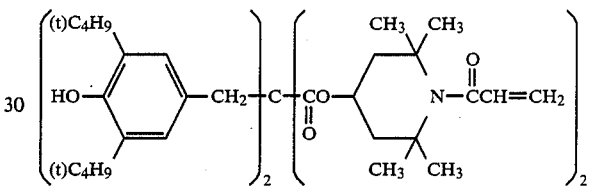

The color printing paper prepared in the above-described way was exposed to light through a wedge (1/10 second, 10 CMS), and then, after subjecting to Processing steps A and B indicated in Table 2, the magenta color developed image density was measured, in which case the fogged exposure (0.5 lux on the photosensitive material film, color temperature 5400° K.) was made for 5 seconds after 15 seconds from the initiation of the development during the color development.

The results obtained are shown in Table 3.

TABLE 2

| Processing Step A | Time | Temperature | Processing step B |
|---|---|---|---|
| Color development | 1 min 30 sec | 37° C. | The same as Processing A except that benzyl alcohol and diethylene glycol were removed from color developing solution |
| Bleach. fix | 40 sec | 37° C. | |
| Stabilization (1) | 20 sec | 37° C. | |
| Stabilization (2) | 20 sec | 37° C. | |
| Stabilization (3) | 20 sec | 37° C. | |

As the replenishment system of the stabilizing bathes there was adopted the so-called counter current replenishment system in which stabilizing bath (3) is replenished, the solution overflowed from stabilizing bath (3) is led to stabilizing bath (2), and the solution overflowed from stabilizing bath (2) is led to stabilizing bath (1).

| | Mother liquor |
|---|---|
| [Color developing solution] | |
| Diethyleneaminepentaacetic acid | 2.0 g |
| Benzyl alcohol | 12.8 g |
| Diethylene glycol | 3.4 g |
| Sodium sulfite | 2.0 g |

| -continued | |
|---|---|
| | Mother liquor |
| Sodium bromide | 0.26 g |
| Hydroxylamine sulfate | 2.60 g |
| Sodium chloride | 3.20 g |
| 3-Methyl-4-amino-N-ethyl-N-(β-methane-sulfonamidoethyl)-aniline | 4.25 g |
| Potassium carbonate | 30.0 g |
| Fluorescent whitening agent (stilbene series) | 1.0 g |
| Water to make | 1000 ml |
| pH | 10.20 |
| pH was adjusted with potassium hydroxide or hydrochloric acid. | |
| [Bleach. fix solution] | |
| Ammonium thiosulfate | 110 g |
| Sodium hydrogen sulfite | 10 g |
| Ammonium iron (III) diethylenetri-aminepentaacetate (monohydrate) | 56 g |
| Disodium ethylenediaminetetraacetate (dihydrate) | 5 g |
| 2-Mercapto-1,3,4-triazole | 0.5 g |
| Water to make | 1000 ml |
| pH | 6.5 |
| pH was adjusted with aqueous ammonia or hydrochloric acid. | |
| [Stabilizing solution] | |
| 1-Hydroxyethylidene-1,1'-diphosphonic acid (60%) | 1.6 ml |
| Bismuth chloride | 0.35 g |
| Polyvinylpyrrolidone | 0.25 g |
| Aqueous ammonia | 2.5 ml |
| Trisodium nitrilotriacetate | 1.0 g |
| 5-Chloro-2-methyl-4-isothiazoline-3-on | 50 mg |
| 2-Octyl-4-isothiazoline-3-on | 50 mg |
| Fluorescent whitening agent (4,4'-diamino-stilbene series) | 1.0 g |
| Water to make | 1000 ml |
| pH | 7.5 |
| pH was adjusted with potassium hydroxide or hydrochloric acid. | |

TABLE 3

| No. | Nucleation promotor*1 | Processing step A | | Processing step B | |
|---|---|---|---|---|---|
| | | Dmax | Dmin | Dmax | Dmin |
| 1 | Illustrative compound 1 | 2.3 | 0.10 | 2.1 | 0.09 |
| 2 | Illustrative compound 7 | 2.3 | 0.10 | 2.1 | 0.09 |
| 3 | Illustrative compound 26 | 2.4 | 0.10 | 2.2 | 0.09 |
| 4 | Illustrative compound 42 | 2.3 | 0.10 | 2.1 | 0.09 |
| 5 | Illustrative compound 43 | 2.4 | 0.10 | 2.1 | 0.09 |
| 6 | Illustrative compound 50 | 2.3 | 0.10 | 2.1 | 0.09 |
| 7 | Illustrative compound 67 | 2.3 | 0.10 | 2.1 | 0.09 |
| 8 | Illustrative compound 71 | 2.3 | 0.10 | 2.1 | 0.09 |
| 9 | Illustrative compound 83 | 2.3 | 0.10 | 2.1 | 0.09 |
| 10 | No addition | 1.4 | 0.15 | 0.6 | 0.14 |

Amount used $2.0 \times 10^{-4}$ mol/mol Ag

Sample Nos. 1 to 9 which contain the nucleation promoters of this invention showed small variations in $D_{max}$ between the processing step A and processing step B lacking benzyl alcohol as compared with Sample No. 10 containing no nucleation promoter.

With cyan or yellow coloring density also the same results were obtained.

Color printing paper was prepared in the same manner as in Example 1 except that the third layer was prepared so as to have the constitution shown in Table 4, and $5.0 \times 10^{-5}$ mol/mol Ag of a nucleating agent (N-II-7) and nucleation promoters indicated in Table 5 were added to the first, the third, and the fifth layers.

TABLE 4

| The third layer (Green-sensitive layer) | Emulsion A Silver: | | 0.39 g/m² |
| | Gelatin | | 1.56 g/m² |
| | Magenta coupler | (o) | 4.60 × 10⁻⁴ mol/m² |
| | Color image stabilizer | (p) | 0.14 g/m² |
| | Solvent | (q) | 0.42 g/m² |
| | Development accelerator Nucleating agent and nucleation promotor | (d) | 32 mg/m² |

(o) Magenta coupler: (M-2)
(p) Color image stabilizer:
2:3 Mixture (weight ratio) of

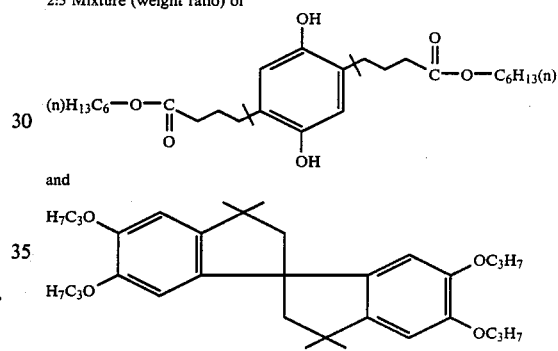

and (q) Solvent:
1:2:2 Mixture (weight ratio) of

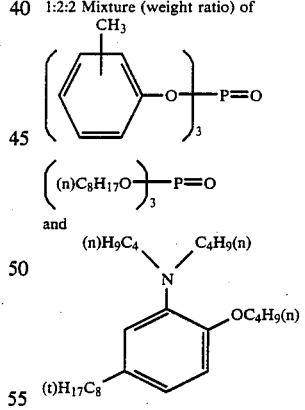

and

Positive images were obtained by carrying out the exposure processing in the same manner as in Example 1 except that the fogging light at the time of color development was removed. The yellow density was measured with the results being shown in Table 5.

TABLE 5

| No. | Nucleation promoter | | Processing Step A | | Processing Step B | | Processing Step C | | Processing Step D | | Processing Step E | | Processing Step F | |
|---|---|---|---|---|---|---|---|---|---|---|---|---|---|---|
| | | | Dmax | Dmin | Dmax | Dmin | Dmax | Dmin | Dmax | Dmin | Dmax | Dmin | Dmax | Dmin |
| 11 | Illustrative compound | 6 | 2.3 | 0.10 | 2.1 | 0.09 | 2.3 | 0.10 | 2.1 | 0.09 | 2.1 | 0.10 | 2.0 | 0.09 |
| 12 | Illustrative | 28 | 2.4 | 0.10 | 2.1 | 0.09 | 2.3 | 0.10 | 2.1 | 0.09 | 2.1 | 0.10 | 2.0 | 0.09 |

TABLE 5-continued

| No. | Nucleation promoter | | Processing Step A | | Processing Step B | | Processing Step C | | Processing Step D | | Processing Step E | | Processing Step F | |
|---|---|---|---|---|---|---|---|---|---|---|---|---|---|---|
| | | | Dmax | Dmin | Dmax | Dmin | Dmax | Dmin | Dmax | Dmin | Dmax | Dmin | Dmax | Dmin |
| 13 | Illustrative compound | 42 | 2.3 | 0.10 | 2.1 | 0.09 | 2.3 | 0.10 | 2.1 | 0.09 | 2.1 | 0.10 | 2.0 | 0.09 |
| 14 | Illustrative compound | 47 | 2.4 | 0.10 | 2.1 | 0.09 | 2.3 | 0.10 | 2.1 | 0.09 | 2.1 | 0.10 | 2.0 | 0.09 |
| 15 | Illustrative compound | 51 | 2.4 | 0.10 | 2.1 | 0.09 | 2.3 | 0.10 | 2.1 | 0.09 | 2.2 | 0.10 | 2.0 | 0.09 |
| 16 | Illustrative compound | 56 | 2.4 | 0.10 | 2.1 | 0.09 | 2.3 | 0.10 | 2.0 | 0.09 | 2.1 | 0.10 | 2.0 | 0.09 |
| 17 | Illustrative compound | 62 | 2.3 | 0.10 | 2.1 | 0.09 | 2.3 | 0.10 | 2.1 | 0.09 | 2.1 | 0.10 | 2.0 | 0.09 |
| 18 | Illustrative compound | 66 | 2.3 | 0.10 | 2.1 | 0.09 | 2.3 | 0.10 | 2.1 | 0.09 | 2.1 | 0.10 | 2.0 | 0.09 |
| 19 | Illustrative compound | 68 | 2.3 | 0.10 | 2.1 | 0.09 | 2.3 | 0.10 | 2.1 | 0.09 | 2.1 | 0.10 | 2.0 | 0.09 |
| 20 | Illustrative compound | 69 | 2.3 | 0.10 | 2.1 | 0.09 | 2.3 | 0.10 | 2.1 | 0.09 | 2.1 | 0.10 | 2.0 | 0.09 |
| 21 | Illustrative compound | 75 | 2.3 | 0.10 | 2.1 | 0.09 | 2.3 | 0.10 | 2.1 | 0.09 | 2.1 | 0.10 | 2.0 | 0.09 |
| 22 | Illustrative compound | 83 | 2.3 | 0.10 | 2.1 | 0.09 | 2.3 | 0.10 | 2.1 | 0.09 | 2.1 | 0.10 | 2.0 | 0.09 |
| 23 | Illustrative compound | 88 | 2.3 | 0.10 | 2.1 | 0.09 | 2.3 | 0.10 | 2.1 | 0.09 | 2.1 | 0.10 | 2.0 | 0.09 |
| 24 | Comparative compound | 1 | 0.7 | 0.13 | 0.2 | 0.12 | 1.0 | 0.13 | 0.5 | 0.12 | 1.7 | 0.13 | 1.5 | 0.13 |
| 25 | Comparative compound | 2 | 0.7 | 0.13 | 0.2 | 0.12 | 1.0 | 0.13 | 0.5 | 0.12 | 1.7 | 0.13 | 1.5 | 0.13 |
| 26 | Comparative compound | 3 | 0.7 | 0.13 | 0.2 | 0.12 | 1.0 | 0.13 | 0.5 | 0.12 | 1.7 | 0.13 | 1.5 | 0.13 |
| 27 | No addition | | 0.7 | 0.13 | 0.2 | 0.12 | 1.0 | 0.13 | 0.5 | 0.12 | 1.7 | 0.13 | 1.5 | 0.13 |

Comparative compound-1

Comparative compound-2

Comparative compound-3

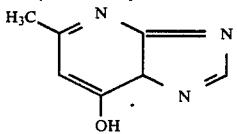

*1 Amount used $4.1 \times 10^{-4}$ mol/mol Ag

Processing steps C and E are the same as Processing step A except that the pH of the color developing solution was made 11.2 and 12.0, respectively, and the time of development was 50 seconds.

Processing steps D and F are the same as Processing step B except that the pH of the color developing solution was made 11.2 and 12.0, respectively, and the time of development was 50 seconds.

When comparing Processing steps A and B in which the pH of the color developing solution is 10.2 or processing steps C and D in which the pH of the color developing solution is 11.2, it is found that Sample Nos. 11 to 23 containing the nucleation promoters of this invention show that the lowering of the maximum image density is only small even in the absence of benzyl alcohol as compared with Sample Nos. 24 to 26 in Comparative Examples. However, in comparison of Processing steps E and F in the case of pH being 12.0 no distinct difference was recognized.

EXAMPLE 3

Color printing paper was prepared in the same manner as in Example 1 except that as cyan coupler, yellow coupler, and magenta coupler the compounds as described below were used, and further, as nucleation promoters those described in Table 6 were used.

| Cyan coupler | 1:1 mixture (mol ratio) of (C-1) and (C-5) |
|---|---|
| Magenta coupler | (M-5) |
| Yellow coupler | (Y-9) |

The color printing paper thus obtained was exposed to light, and then, by subjecting to the same processing step as Processing step B in Example 1 except the pH of the color developing solution, direct positive color images were obtained. The magenta maximum image density of these images was measured with the results being shown in Table 6.

TABLE 6

| No. | Nucleation promoter | | pH of color developing solution | | |
|---|---|---|---|---|---|
| | | | 10.0 | 10.2 | 10.4 |
| 28 | Illustrative compound | -15 | 2.3 | 2.4 | 2.4 |
| 29 | Illustrative compound | -30 | 2.3 | 2.4 | 2.4 |

TABLE 6-continued

| | | pH of color developing solution | | |
|---|---|---|---|---|
| No. | Nucleation promoter | 10.0 | 10.2 | 10.4 |
| 30 | Illustrative compound -43 | 2.4 | 2.4 | 2.4 |
| 31 | Comparative compound -4 | 1.5 | 1.8 | 2.1 |
| 32 | No addition | 1.5 | 1.8 | 2.1 |

Comparative compound-4

Amount used 4.8 × 10$^{-4}$ mol/mol Ag

Sample Nos. 28 to 30 containing the nucleation promoters of this invention were found preferable in the point that the variation in the maximum image density due to the change in pH was small as compared with Sample No. 31 and No. 32.

With cyan or yellow coloring density also the same results were obtained.

Further, with Illustrative compounds 1, 3, 6, 13, 23, 26, 28, 36, 42, 56, 62, 67, 76, 83, 89, 90, 95, and 99 used an nucleation promoters also the same results were obtained.

EXAMPLE 4

Color printing paper was prepared in the same manner as in Example 2 except that using 3.5×10$^{-5}$ mol/ol Ag of nucleating agent (N-II-17) together with nucleation promoters described in Table 7, the cyan coupler (C-4) was used.

This color printing paper, after having been stored for three days (incubation) in an environment of 40° C. and 80% R. H., was subjected to Processing steps A and B in Example 2. The maximum yellow density of the direct positive color images thus obtained was measured, with the results being shown in Table 7.

TABLE 7

| | | Processing step A Incubation | | Processing step B Incubation | |
|---|---|---|---|---|---|
| No. | Nucleation promoter | absent | present | absent | present |
| 33 | Illustrative compound 7 | 2.3 | 2.1 | 2.1 | 2.0 |
| 34 | Illustrative compound 13 | 2.2 | 2.1 | 2.1 | 2.0 |
| 35 | Illustrative compound 28 | 2.4 | 2.1 | 2.2 | 2.0 |
| 36 | Illustrative compound 31 | 2.2 | 2.1 | 2.1 | 2.0 |
| 37 | Illustrative compound 42 | 2.3 | 2.2 | 2.1 | 2.1 |
| 38 | Illustrative compound 56 | 2.2 | 2.1 | 2.1 | 1.9 |
| 39 | Illustrative compound 59 | 2.2 | 2.1 | 2.1 | 1.9 |
| 40 | Illustrative compound 62 | 2.3 | 2.1 | 2.1 | 2.0 |
| 41 | Illustrative compound 76 | 2.2 | 2.0 | 2.1 | 1.9 |
| 42 | Illustrative compound 83 | 2.2 | 2.1 | 2.0 | 1.9 |
| 43 | Illustrative compound 95 | 2.3 | 2.1 | 2.1 | 2.0 |
| 44 | Illustrative compound 99 | 2.3 | 2.0 | 2.1 | 1.9 |
| 45 | Bi addutuib | 0.9 | 0.6 | 0.8 | 0.1 |

*1 Amount used 4.2 × 10$^{-4}$ mol/mol Ag

Sample Nos. 33 to 44 containing the nucleation promoters of this invention show that the lowering of D$_{max}$ due to incubation is small as compared with Comparative Example No. 45, and moreover, such as effect of improvement is more marked in Processing step B containing no benzyl alcohol.

EXAMPLE 5

By the observation of the direct positive color images obtained in Example 3 it was found that Sample Nos. 28 to 30 containing the nucleation promoters of this invention had fewer second reversal negative images than Comparative Example Nos. 31 and 32.

EXAMPLE 6

Color printing paper was prepared in the same manner as in Example 3 except that using 4.2×10$^{-6}$ mol/mol Ag of nucleating agent (N-I-9), the nucleation promoter was omitted.

Direct positive color images were obtained by carrying out the exposure processing in the same manner as in Example 2 except that each 4.2×10$^{-6}$ mol/liter of nucleation promoters described in Table 8 were added to the color developing solution.

The magenta coloring density was measured with the results being shown in Table 8.

TABLE 8

| | | Processing step A | | Processing step B | |
|---|---|---|---|---|---|
| No. | Nucleation promoter | D$_{max}$ | D$_{min}$ | D$_{max}$ | D$_{min}$ |
| 46 | Illustrative compound 28 | 2.4 | 0.10 | 2.2 | 0.09 |
| 47 | Illustrative compound 43 | 2.3 | 0.10 | 2.1 | 0.09 |
| 48 | Illustrative compound 56 | 2.4 | 0.10 | 2.2 | 0.09 |
| 49 | Illustrative compound 83 | 2.4 | 0.10 | 2.2 | 0.09 |
| 50 | Comparative compound 1 | 1.6 | 0.13 | 1.0 | 0.12 |
| 51 | No addition | 1.6 | 0.13 | 1.0 | 0.12 |

As obvious from the results shown in Table 8 it is found that even when the nucleation promoters are added to the color developing solution, the same results as in Example 2 are obtained.

EXAMPLE 7

Color photosensitive material was prepared in the same manner as in Example 1 except that 3.1×10$^{-5}$ mol/mol Ag of nucleating agent (N-II-9) and each 2.1×10$^{-4}$ mol/mol Ag of nucleation promoters described in Table 9 were added to the first, third, and fifth layers, and these layers were coated on polyethylene terephthalate film provided with an antihalation layer on the back side with the coating weights of the first, third, and fifth layers being respectively increased by 1.5 times. After the color developing solution was used at 35° C. for 16 hours in a running operation. Processing steps A and B in Example 2 were carried out, and the sensitivity of the second reversal negative images (represented as the relative value of the reciprocal of the light exposure giving a density 0.2) was measured with the results being shown in Table 9.

TABLE 9

| | | Processing step A Running | | Processing step B Running | |
|---|---|---|---|---|---|
| No. | Nucleation promoter | 0 hour | 16 hours | 0 hour | 16 hours |
| 53 | Illustrative compound 6 | 20 | 20 | 30 | 30 |
| 54 | Illustrative compound 28 | 20 | 20 | 25 | 25 |
| 55 | Illustrative compound 56 | 20 | 30 | 30 | 30 |
| 55 | Illustrative compound 83 | 30 | 30 | 30 | 35 |
| 57 | Illustrative compound 95 | 20 | 20 | 30 | 30 |
| 58 | Illustrative compound 99 | 30 | 30 | 30 | 30 |

TABLE 9-continued

| | | Processing step A Running | | Processing step B Running | |
|---|---|---|---|---|---|
| No. | Nucleation promoter | 0 hour | 16 hours | 0 hour | 16 hours |
| 59 | No addition | 100 Standard | 130 | 180 | 300 |

As obvious from the results shown in Table 9, it is found that in Sample Nos. 53 to 58 containing the nucleation promoters of this invention the sensitivity increase in the second reversal negative image due to the running deterioration especially in Processing step B containing no benzyl alcohol is preferably small as compared with Comparative Example No. 59.

EXAMPLE 8

The procedure in Example 1 was repeated except that use was made of the nucleation promoters as shown in Table 10. The results are shown in Table 10.

TABLE 10

| | | Processing step A | | Processing step B | |
|---|---|---|---|---|---|
| No. | Nucleation promoter | Dmax | Dmin | Dmax | Dmin |
| 60 | Illustrative compound 106 | 2.2 | 0.11 | 2.0 | 0.09 |
| 61 | Illustrative compound 110 | 2.2 | 0.11 | 2.1 | 0.09 |
| 62 | Illustrative compound 112 | 2.3 | 0.11 | 2.1 | 0.09 |
| 63 | Illustrative compound 114 | 2.2 | 0.11 | 2.0 | 0.09 |
| 64 | Illustrative compound 121 | 2.2 | 0.11 | 2.0 | 0.09 |
| 65 | Comparative compound 1 | 1.4 | 0.11 | 0.6 | 0.14 |
| 66 | No addition | 1.4 | 0.15 | 0.6 | 0.14 |

*Amount used $1.5 \times 10^{-4}$ mol/mol Ag

Comparative compound - 1

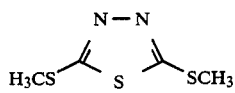

Comparative compound 2

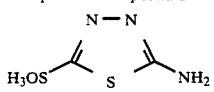

Comparative compound 3

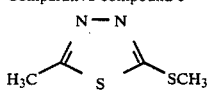

Sample Nos. 60 to 64 containing the nucleation promoters of this invention showed that the variations in $D_{max}$ between Processing step A and Processing step B deprived of benzyl alcohol were small as compared with No. 65 containing Comparative compound or No. 66 containing no nucleation promoter.

With cyan or yellow coloring density also the same results were obtained.

EXAMPLE 9

Color printing paper was prepared in the same manner as in Example 2 except that using a yellow coupler as described below, $5.0 \times 10^{-5}$ mol/mol Ag of a nucleating agent (N-II-4) and nucleation promoters shown in Table 11 were added to the first, third, and fifth layers.

(n) Yellow coupler

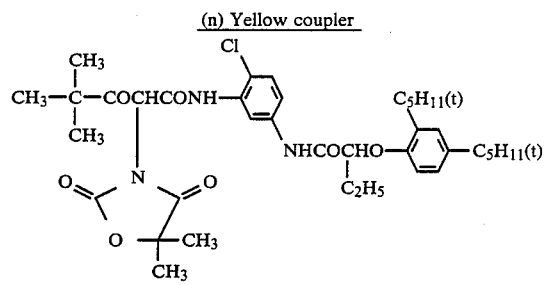

Positive images were obtained by carrying out the exposure processing in the same manner as in Example 1 except that the fogging light at the time of color development was removed. The yellow density was measured with the results being shown in Table 11.

TABLE 11

| No. | Nucleation prometer* | Processing step A | | Processing step B | | Processing step C | | Processing step D | | Processing step E | | Processing step F | |
|---|---|---|---|---|---|---|---|---|---|---|---|---|---|
| | | Dmax | Dmin | Dmax | Dmin | Dmax | Dmin | Dmax | Dmin | Dmax | Dmin | Dmax | Dmin |
| 67 | Illustrative compound 107 | 2.2 | 0.10 | 2.0 | 0.09 | 2.2 | 0.10 | 2.0 | 0.09 | 2.1 | 0.10 | 2.0 | 0.09 |
| 68 | 109 | 2.2 | 0.10 | 2.0 | 0.09 | 2.2 | 0.10 | 2.0 | 0.09 | 2.1 | 0.10 | 1.9 | 0.09 |
| 69 | 110 | 2.1 | 0.10 | 1.9 | 0.09 | 2.2 | 0.10 | 2.0 | 0.09 | 2.1 | 0.10 | 1.9 | 0.09 |
| 70 | 113 | 2.2 | 0.10 | 2.0 | 0.09 | 2.2 | 0.10 | 2.0 | 0.09 | 2.1 | 0.10 | 1.9 | 0.09 |
| 71 | 118 | 2.2 | 0.10 | 2.0 | 0.09 | 2.2 | 0.10 | 2.0 | 0.09 | 2.1 | 0.10 | 2.0 | 0.09 |
| 72 | 122 | 2.2 | 0.10 | 2.0 | 0.09 | 2.2 | 0.10 | 2.0 | 0.09 | 2.1 | 0.10 | 1.9 | 0.09 |
| 73 | 124 | 2.2 | 0.10 | 2.0 | 0.09 | 2.2 | 0.10 | 1.9 | 0.09 | 2.1 | 0.10 | 2.0 | 0.09 |
| 74 | Comparative compound 1 | 0.7 | 0.13 | 0.2 | 0.12 | 1.0 | 0.13 | 0.5 | 0.12 | 1.7 | 0.13 | 1.5 | 0.13 |
| 75 | 2 | 0.7 | 0.13 | 0.2 | 0.12 | 1.0 | 0.13 | 0.5 | 0.12 | 1.7 | 0.13 | 1.5 | 0.13 |
| 76 | 3 | 0.7 | 0.13 | 0.2 | 0.12 | 1.0 | 0.13 | 0.5 | 0.12 | 1.7 | 0.13 | 1.5 | 0.13 |
| 77 | No addition | 0.7 | 0.13 | 0.2 | 0.12 | 1.0 | 0.13 | 0.5 | 0.12 | 1.7 | 0.13 | 1.5 | 0.13 |

(N-II-4)

1-Formyl-2-[4-(3-(5-mercaptotetrazole-1-yl)-pehnyl-]ureido)phenyl]hydrazine

Processing steps C and E are the same as Processing step A except that the pH of the color developing solution was made 11.2 and 12.0, respectively, and the time of development was 50 seconds.

Processing steps D and F are the same as Processing step B except that the pH of the color developing solution was made 11.2 and 12.0, respectively, and the time of development was 50 seconds.

When comparing Processing steps A and B in which the pH of the color developing solution is 10.2 or Processing steps C and D in which the pH of the color developing solution is 11.2, it is found that Sample Nos. 67 to 73 containing the nucleation promoters of this invention show that the lowering of the maximum image density is only small even in the absence of benzyl alcohol as compared with Comparative Example Nos. 74 to 76. However, in comparison of Processing steps E and F in the case of pH being 12.0 no distinct difference was recognized.

EXAMPLE 10

Color printing paper was prepared in the same manner as in Example 1 except that as cyan coupler, yellow coupler, and magenta coupler the following were used, and further, as nucleation promoter those described in Table 12 were used.

| Cyan coupler | 1:1 mixture (mol ratio) of (C-5) and (C-1) |
| Magenta coupler | (M-15) |
| Yellow coupler | (Y-9) |

The color printing paper thus obtained was exposed to light, and then, by subjecting to the same processing as Processing step B in Example 1 except the pH of the color developing solution, direct positive color images were obtained. The magenta maximum image density of these images was measured with the results being shown in Table 12.

TABLE 12

| | | pH of color developing solution | | |
| No. | Nucleation promoter* | 10.0 | 10.2 | 10.4 |
| 78 | Illustrative compound-107 | 2.1 | 2.2 | 2.2 |
| 79 | Illustrative compound-110 | 2.1 | 2.3 | 2.3 |
| 80 | Illustrative compound-114 | 2.1 | 2.2 | 2.3 |
| 81 | Comparative compound-1 | 1.5 | 1.8 | 2.1 |
| 82 | No addition | 1.5 | 1.8 | 2.1 |

*Amount used $2.5 \times 10^{-4}$ mol/mol Ag.

Sample Nos. 78 to 80 containing the nucleation promoters of this invention were found preferable in the point that the variation in the maximum image density due to the change in pH was small as compared with Sample Nos. 81 and 82.

With cyan or yellow coloring density also the same results were obtained.

Further, with Illustrative compounds 106, 108, 109, 111–113, 115–125 used as nucleation promoters also the same results were obtained.

EXAMPLE 11

Color printing paper was prepared in the same manner as in Example 9 except that using the cyan coupler described below, $3.5 \times 10^{-5}$ mol/mol Ag of a nucleating agent (N-II-3) was used together with nucleation promoters described in Table 13.

Cyan coupler

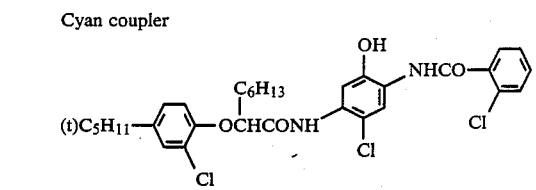

This color printing paper, after having been stored for three days (incubation) in an environment of 40° C. and 80% R. H., was subjected to Processing steps A and B in Example 2. The maximum yellow density of the direct positive color images was measured with the results being shown in Table 13.

TABLE 13

| | | Processing step A Incubation | | Processing step B Incubation | |
| No. | Nucleation promoter* | Absent | Present | Absent | Present |
| 83 | Illustrative compound 107 | 2.2 | 2.0 | 2.1 | 1.9 |
| 84 | Illustrative compound 113 | 2.1 | 2.0 | 2.0 | 1.9 |
| 85 | Illustrative compound 123 | 2.2 | 2.0 | 2.1 | 1.9 |
| 86 | Comparative compound 2 | 0.8 | 0.6 | 0.5 | 0.1 |
| 87 | No addition | 0.8 | 0.6 | 0.5 | 0.1 |

*Amount used $1.5 \times 10^{-4}$ mol/mol Ag.

(N-II-3)

1-Formyl-2-{4-[3-(5-mercaptotetrazole-1-yl)}phenyl)ureido phenyl}hydrazine.

Sample Nos. 83 to 85 containing the nucleation promoters of this invention show that the lowering of $D_{max}$ due to incubation is small as compared with Comparative Example No. 86, and moreover, such an effect of improvement is more marked in Processing step B containing no benzyl alcohol.

EXAMPLE 12

By the observation of the direct positive color images obtained in Example 10, it was found that Sample Nos. 78 to 80 containing the nucleation promoters of this invention had fewer second reversal negative images than Comparative Example No. 81 or No. 82.

EXAMPLE 13

Color printing paper was prepared in the same manner as in Example 3 except that using $4.2 \times 10^{-6}$ mol/mol Ag of nucleating agent (N-I-5), the nucleation promoter was omitted.

Direct positive color images were obtained by carrying out the exposure processing in the same manner as in Example 9 except that each $4.0 \times 10^{-5}$ mol/liter of nucleation promoters described in Table 14 were added to the color developing solution.

The magenta coloring density was measured with the results being shown in Table 14.

TABLE 14

| No. | Nucleation promoter | Processing step A | | Processing step B | |
|---|---|---|---|---|---|
| | | $D_{max}$ | $D_{min}$ | $D_{max}$ | $D_{min}$ |
| 88 | Illustrative compound-106 | 2.3 | 0.10 | 2.1 | 0.09 |
| 89 | Illustrative compound-109 | 2.3 | 0.10 | 2.0 | 0.09 |
| 90 | No addition | 1.6 | 0.13 | 1.0 | 0.12 |

(N-I-5)

6-Ethoxythiocarbonylamino-2-methyl-1propargyl-quinolium trifluoromethansulfonate As obvious from the results shown in Table 14, it is found that even when the nucleation promoters are added to the color developing solution, the same results as in Example 2 are obtained.

EXAMPLE 14

Color photosensitive material was prepared in the same manner as in Example 8 except that $3.1 \times 10^{-5}$ mol/mol Ag of nucleating agent (N-II-9) and each $2.1 \times 10^{-4}$ mol/mol Ag of nucleation promoters Nos. 106 to 115 and 120 to 125 were added to the first, third, and fifth layers, and these layers were coated on polyethylene terephthalate film provided with an antihalation layer on the back side with the coating weights of the first, third, and fifth layers being respectively increased by 1.5 times. After the color developing solution was used at 35° C. for 16 hours in a running operation, Processing steps A and B in Example 9 were carried out, and the sensitivity of the second reversal negative images (represented as the relative value of the reciprocal of the light exposure giving a density 0.2) was measured.

(N-II-9)

2-[4-{3-[N-(benzotriazole-5-carboxamido)carbamoyl]-propanamido}phenyl]-1-formylhydrazine Samples containing each of the illustrative compounds 106–115 and 120–125 which are the nucleation promoters of this invention, were preferably small in the sensitivity of the second reversal negative image as compared with Samples containing no nucleation promoter, and moreover, this tendency was found to be more marked in Processing step B containing no benzyl alcohol.

EXAMPLE 15

The procedure in Example 1 was repeated except that the nucleation promoters described in Table 16 were used. The results obtained are shown in Table 16.

TABLE 15

| No. | Nucleation promoter* | Processing step A | | Processing step B | |
|---|---|---|---|---|---|
| | | $D_{max}$ | $D_{min}$ | $D_{max}$ | $D_{min}$ |
| 91 | Illustrative compound 126 | 2.2 | 0.10 | 2.0 | 0.09 |
| 92 | 129 | 2.3 | 0.10 | 2.1 | 0.09 |
| 93 | 137 | 2.2 | 0.10 | 2.0 | 0.09 |
| 94 | 138 | 2.2 | 0.10 | 2.0 | 0.09 |
| 95 | Comparative compound 1 | 1.4 | 0.15 | 0.6 | 0.14 |
| 96 | No addition | 1.4 | 0.15 | 0.6 | 0.14 |

*Amount used $1.5 \times 10^{-4}$ mol/mol Ag.
Comparative compound 1

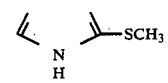

Sample Nos. 91 to 94 containing the nucleation promoters of this invention showed that the variation in $D_{max}$ between Processing step A and Processing step B deprived of benzyl alcohol were small as compared with No. 95 containing Comparative compound or No. 96 containing no nucleation promoter.

With cyan or yellow coloring density also the same results were obtained.

EXAMPLE 16

Color printing paper was prepared in the same manner as in Example 2 except that $5.0 \times 10^{-5}$ mol/mol Ag of nucleating agent (N-II-7) and nucleation promoters as shown in Table 16 were added to the first, third, and fifth layers.

Positive images were obtained by carrying out the exposure processing in the same manner as in Example 2 except that the fogging light at the time of color development was removed. The yellow density was measured with the results being shown in Table 16.

TABLE 16

| No. | Nucleation prometer* | Processing step A | | Processing step B | | Processing step C | | Processing step D | | Processing step E | | Processing step F | |
|---|---|---|---|---|---|---|---|---|---|---|---|---|---|
| | | Dmax | Dmin | Dmax | Dmin | Dmax | Dmin | Dmax | Dmin | Dmax | Dmin | Dmax | Dmin |
| 97 | Illustrative compound 129 | 2.3 | 0.10 | 2.1 | 0.09 | 2.3 | 0.10 | 2.1 | 0.09 | 2.1 | 0.10 | 2.0 | 0.09 |
| 98 | 137 | 2.3 | 0.10 | 2.0 | 0.09 | 2.3 | 0.10 | 2.0 | 0.09 | 2.1 | 0.10 | 1.9 | 0.09 |
| 99 | 140 | 2.3 | 0.10 | 2.1 | 0.09 | 2.3 | 0.10 | 2.1 | 0.09 | 2.1 | 0.10 | 2.0 | 0.09 |
| 100 | Comparative compound 2 | 0.7 | 0.13 | 0.2 | 0.12 | 1.0 | 0.13 | 0.5 | 0.12 | 1.7 | 0.13 | 1.5 | 0.13 |
| 101 | No addition | 0.7 | 0.13 | 0.2 | 0.12 | 1.0 | 0.13 | 0.5 | 0.12 | 1.7 | 0.13 | 1.5 | 0.13 |

*Amount used $1.8 \times 10^{-4}$ mol/mol Ag
Comparative compound 2

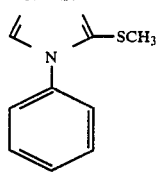

(N-II-7)

1-Formyl-2-[4-{3-[N-(5-mercapto-1,3,4-thiadiazole-2-yl)carbamoyl]-propanamido}phenyl]hydrazine

EXAMPLE 17

Color printing paper was prepared in the same manner as in Example 15 except that as cyan coupler, yellow coupler, and magenta coupler, the compounds as described below and further, as nucleation promoter the compounds described in Table 17 were used.

| Cyan coupler | 1:1 Mixture of (C-1) and (C-5) (mol ratio) |
|---|---|
| Magenta coupler | (M-15) |
| Yellow coupler | (Y-9) |

After this color printing paper was exposed to light, direct positive color images were obtained in the same processing step as Processing step B in Example 15 except the pH of the color developing solution. The magenta maximum image density of these images was measured with the results being shown in Table 17.

TABLE 17

| | | Processing step B | | |
|---|---|---|---|---|
| No. | Nucleation promoter* | pH 10.0 | pH 10.2 | pH 10.4 |
| 102 | Illustrative compound 126 | 2.0 | 2.2 | 2.3 |
| 103 | 135 | 2.0 | 2.1 | 2.3 |
| 104 | Comparative compound 3 | 1.4 | 1.8 | 2.0 |
| 105 | No addition | 1.5 | 1.7 | 2.1 |

*Amount used 7.8 × 10$^{-5}$ mol/mol Ag.
Comparative compound 3

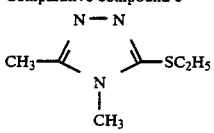

In Sample No. 102 and No. 103 the variations in the maximum image density due to the change in pH were preferably small as compared with No. 104 and No. 105.

With cyan or yellow coloring density also the same results were obtained.

Further, with Illustrative compounds 127 to 134, 136, 138, and 139 used as nucleation promoters also the same results were obtained.

EXAMPLE 18

Color printing paper was prepared in the same manner as in Example 16 except for using 3.5 × 10$^{-5}$ mol/mol Ag of nucleating agent (N-II-3), nucleation promoters described in Table 18, and cyan coupler (C-4).

This printing paper was stored for three days incubation in an environment of 40° C. and 80% R. H., and then subjected to Processing steps A and B in Example 16. The maximum yellow density of the direct positive color images was measured with the results being shown in Table 20.

TABLE 18

| | | Processing step A Incubation | | Processing step B Incubation | |
|---|---|---|---|---|---|
| No. | Nucleation promoter* | Absent | Present | Absent | Present |
| 106 | Illustrative compound-128 | 2.2 | 2.0 | 2.1 | 2.0 |
| 107 | Illustrative | 2.2 | 2.0 | 2.1 | 1.9 |

TABLE 18-continued

| | | Processing step A Incubation | | Processing step B Incubation | |
|---|---|---|---|---|---|
| No. | Nucleation promoter* | Absent | Present | Absent | Present |
| | compound-135 | | | | |
| 108 | Comparative compound-3 | 0.9 | 0.6 | 0.5 | 0.1 |
| 109 | No addition | 0.9 | 0.6 | 0.5 | 0.1 |

*Amount used 3.8 × 10$^{-4}$ mol/mol Ag.

(N-II-3)

1-Formyl-2-{4-[3-(5-mercaptotetrazole-lyl)phenyl]-ureido}hydrazine.

In sample No. 106 and No. 107 containing the nucleation promoters of this invention the lowering of D$_{max}$ due to incubation was small as compared with Comparative Example No. 108, and moreover, such as effect of improvement was more marked in Processing step B containing no benzyl alcohol.

EXAMPLE 19

By the observation of the direct positive color images obtained in Example 17 it was found that Sample No. 102 and No. 103 containing the nucleation promoters of this invention had fewer second reversal negative images than Comparative Example No. 104 and No. 105.

EXAMPLE 20

Color printing paper was prepared in the same manner as in Example 17 except that using 4.2 × 10$^{-6}$ mol/mol Ag of nucleating agent (N-I-5) the nucleation promoter was omitted.

Direct positive color images were obtained by carrying out the exposure processing in the same manner 16 except that each 4.0 × 10$^{-5}$ mol/liter as in Example 16 except that each 4.0 × 10$^{-5}$ mol/liter of nucleation promoters described in Table 19 were added to the color developing solution.

The magenta coloring density was measured with the results being shown in Table 19.

TABLE 19

| | | Processing step A | | Processing step B | |
|---|---|---|---|---|---|
| No. | Nucleation promoter | D$_{max}$ | D$_{min}$ | D$_{max}$ | D$_{min}$ |
| 110 | Illustrative compound-130 | 2.2 | 0.10 | 2.0 | 0.09 |
| 111 | Illustrative compound-140 | 2.2 | 0.10 | 2.0 | 0.09 |
| 112 | Comparative compound-1 | 1.6 | 0.13 | 1.0 | 0.12 |
| 113 | No addition | 1.6 | 0.13 | 1.0 | 0.12 |

(N-I-5)

6-Ethoxythiocarbonylamino-2-methyl-1-propargyl-quinolinium trifluoromethanesulfonate.

As obvious from the results shown in Table 19, it is found that even when the nucleation promoter is added to the color developing solution the same results as in Example 16 are obtained.

EXAMPLE 21

Color photosensitive material was prepared in the same manner as in Example 15 except that 3.1 × 10$^{-5}$ mol/mol Ag of nucleating agent (N-II-9) and each 2.1 × 10$^{-4}$ mol/mol Ag of nucleation promoters Nos. 126, and 128 to 140 were added to the first, third, and fifth layers, and these layers were coated on polyethylene terephthalate film provided with an antihalation layer on the back side with the coating weights to the first, third, and fifth layers being respectively increased by 1.5 times. After the color developing solution was used at 35° C. for 16 hours in a running operation, Processing steps A and B in Example 16 were carried out. The sensitivity (represented as the relative value of the reciprocal of the light exposure giving a density 0.2) of the second reversal negative images was measured.

(N-II-9)

2-[4-{3-N-(benzotriazole-5-carboxamido)carbamoyl]-propanamido}phenyl]-1-formylhydrazine.

All the samples containing Illustrative compounds 126, 128 to 140, which are the nucleation promoters of this invention, showed that the sensitivity of the second reversal negative images were preferably small as compared with samples containing no nucleation promoter, and moreover, this tendency was more marked in Processing step B containing no benzyl alcohol.

EXAMPLE 22

The procedure of Example 2 was repeated except for proceeding a processing step F wherein benzyl alcohol is not used in the processing step F to obtain the same results as Example 2.

EXAMPLE 23

The procedure of Example 1 was repeated except for proceeding a processing step G wherein benzyl alcohol is not used in the processing step G to obtain the same results as Example 1.

EXAMPLE 24

The procedure of Example 2 was repeated except for proceeding a processing step H wherein benzyl alcohol is not used in the processing step H to obtain the same results as Example 2.

| Processing Step F | | |
|---|---|---|
| Step | Time | Temperature (°C.) |
| Color Development | 1 min 30 sec | 38 |
| Bleach-Fix | 40 sec | 35 |
| Rinsing (1) | 40 sec | 30–36 |
| Rinsing (2) | 40 sec | 30–36 |
| Rinsing (3) | 15 sec | |
| Drying | 30 sec | 75–80 |

Rinsing was carried out by supplying replenishing water to rinsing bath (3), supplying over-flowed water therefrom to rinsing bath (2) and supplying overflowed water therefrom to rinsing bath (1), i.e., countercurrent rinsing process. The rinsing water quantity brought from the previous bath was 35 ml per m² of the photosensitive material and thus the used amount of the replenishing water was 9.1 times the volume of the original replenishing water.

| Color Developing Solution | |
|---|---|
| Ethylenediamine tetrakismethylene phosphonic acid | 0.5 g |
| Diethyleneglycol | 8.0 g |
| Benzylalcohol | 12.0 g |
| Sodium bromide | 0.6 g |
| Sodium chloride | 0.5 g |

| -continued | |
|---|---|
| Color Developing Solution | |
| Sodium sulfite | 2.0 g |
| N,N-Diethylhydroxylamine | 3.5 g |
| Triethylenediamine (1,4-diazabicyclo[2,2,2] octane) | 3.5 g |
| 3-Methyl-4-amino-N-ethyl-N-(β-methanesulfonamidoethyl)-aniline sulfate | 5.5 g |
| Potassium carbonate | 30.0 g |
| Fluorescent brightening agent (stilbene series) | 1.0 g |
| Pure water to make | 1000 ml |
| pH adjusted to 10.50 using KOH or HCl. | |

| Bleach Fixing Solution | |
|---|---|
| | Mother liquid = Replenishing Solution |
| Ammonium thiosulfate | 100 g |
| Sodium hydrogensulfite | 21.0 g |
| Ethylenediaminetetraacetic acid iron (III) ammonium (dihydrate) | 50.0 g |
| Ethylenediaminetetraacetic acid disodium (dihydrate) | 5.0 g |
| Pure water to make | 1000 ml |
| pH adjusted to 6.3 using ammonia water and HCl | |
| Rinsing Water | |
| Pure water was used. | |

The term "pure water" as used herein means water wherein density of all kinds of cations other than hydrogen ion and density of all kinds of anions other than hydroxyl ion are reduced to 1 ppm or less.

| Processing Step G | | |
|---|---|---|
| Step | Time (Sec) | Temperature (°C.) |
| Color developement* | 135 | 36 |
| Bleach-Fix | 40 | 36 |
| Stabilization (1) | 40 | 36 |
| Stabilization (2) | 40 | 36 |
| Drying | 40 | 70 |
| Color Developing Solution | | |
| Hydroxyethyliminodiacetate | 0.5 g | |
| β-cyclodextrin | 1.5 g | |
| Monoethyleneglyrol | 9.0 g | |
| Benzylalcohol | 9.0 g | |
| Monoethanol amine | 2.5 g | |
| Sodium bromide | 2.3 g | |
| Sodium chloride | 5.5 g | |
| N,N-Diethyyhydroxylamine | 5.9 g | |
| 3-Methyl-4-amino-N-ethyl-N-(β-methanesulfonamidoethyl)-aniline sulfate | 2.7 g | |
| 3-Methyl-4-amino-N-ethyl-N-(β-hydroxyethyl)-aniline sulfate | 4.5 g | |
| Sodium carbonate | 30.0 g | |
| Fluorescent brightening agent (stilbene series) | 1.0 g | |
| Pure water to make | 1000 ml | |
| pH adjusted to 10.30 g Using KOH or HCl. | | |
| Bleach Fixing Solution | | |
| Ammonium thiosulfate | 110 g | |
| Sodium hydrogensulfite | 12 g | |
| Diethylenetriamine tetraacetic acid iron (III) ammonium | 80 g | |
| Diethylenetriamine tetraacetic acid | 5 g | |
| 2-Mercapto-5-amino-1,3,4-thiadiazole | 0.3 g | |
| Water to make | 1000 ml | |
| pH adjusted to 6.80 | | |

-continued

| Using ammonia water or HCl. | |
|---|---|
| Stabilization Solution | |
| 1-Hydroxyethylidene-1,1-disulfonic acid | 2.7 g |
| β-Phenylphenol | 0.2 g |
| Potassium chloride | 2.5 g |
| Bismuth chloride | 1.0 g |
| Zinc chloride | 0.25 g |
| Sodium sulfite | 0.3 g |
| Ammonium sulfate | 4.5 g |
| Fluorescent brightening agent (stilbene series) | 0.5 g |
| Pure water to make | 1000 ml |
| pH adjusted to 7.2 | |
| Using KOH and HCl. | |

| Processing Step H | | |
|---|---|---|
| Step | Time (sec) | Temperature (°C.) |
| Color development | 70 | 38 |
| Bleach-Fix | 30 | 38 |
| Rinsing (1) | 30 | 38 |
| Rinsing (2) | 30 | 38 |

*Color development was carried out while light-fogging by using a white-light of 1 lux for 15 sec after dipping in a color developing solution for 15 sec.

The used rinsing water is b 8.6 times the original rinsing water.

| Color Development | |
|---|---|
| Diethylenetriaminetetraacetic acid | 0.5 g |
| 1-Hydroxyethylidene-1,1-diphosphonic acid | 0.5 g |
| Diethyleneglycol | 8.0 g |
| Benzyl alcohol | 9.0 g |
| Sodium Bromide | 0.7 g |
| Sodium chloride | 0.5 g |
| Sodium sulfite | 2.0 g |
| Hydroxylamine sulfate | 2.8 g |
| 3-Methyl-4-amino-N-ethyl-N-β-methanesulfonamidoethyl)-aniline sulfate | 2.0 g |
| 3-Methyl-4-amino-N-ethyl-N-(β-hydroxyethyl)-aniline sulfate | 4.0 g |
| Patassium carbonate | 30.0 g |
| Fluorescent brighteniong agent (stilbene series) | 1.0 g |
| Pure water to make | 1000 ml |
| pH adjusted to 10.50 | |
| Using KOH or HCl. | |
| Bleach Fixing Solution | |
| Ammonium thiosulfate | 77 g |
| Sodium hydrogensulfite | 14.0 g |
| Ethylenediaminetetraacetic acid iron (III) ammonium (dihydrate) | 40.0 g |
| Ethylenediaminetetraacetic acid disodium (dihydrate) | 4.0 g |
| 2-Mercapto-1,3,4-triazole | 0.5 g |
| Pure water to make | 1000 ml |
| pH adjusted to 7.0 | |
| Using ammonia water or HCl. | |
| Rinsing Water | |
| Pure water was used (a mother liquid = replenishing water) | |

In accordance with the process of this invention, it is possible to obtain direct positive color images of which the lowering of the coloring density is small even when the processing is carried out in a short period of time using a color developing solution containing substantially no benzyl alcohol.

Further, it is possible to obtain direct positive color images which show little variation in the maximum image density even when the pH of the color developing solution containing substantially no benzyl alcohol changes.

It is also possible to obtain photosensitive materials those storage stability in the raw state has been improved if the nucleation promoters of this invention are contained in them.

Still further, in accordance with the process of this invention direct positive color images can be obtained with the formation of second reversal negative images being lessened when a running processing is carried out by the use of a color developing solution containing substantially no benzyl alcohol.

While the invention has been described in detail and with reference to specific embodiments thereof, it will be apparent to one skilled in the art that various changes and modifications can be made therein without departing from the spirit and scope thereof.

What is claimed is:

1. A process for forming a direct positive color image comprising imagewise exposing a photosensitive material containing at least one emulsion layer of silver halide of internal latent image type, which has not been preliminarily fogged, and a color image-forming coupler; developing said material using a surface developing solution containing an aromatic primary amine color developing agent in the presence of a nucleating agent and/or in the condition that fogging exposure is carried out prior to the developing step or during the developing step; bleaching; and fixing, wherein said color coupler is a compound which is in itself substantially nondiffusible, and capable of forming or releasing a substantially nondiffusible dye upon oxidative coupling with said aromatic primary amine color developing agent and said development processing is carried out at a pH of 11.5 or less using a developing solution containing substantially no benzyl alcohol in the presence of at least one compound selected from the group consisting of the compounds represented by the general formula (I)

General formula (I)

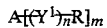

wherein A represents a group being adsorbed on silver halide, $Y^1$ represents a divalent group consisting of an atom or atomic group selected from the group consisting of a nitrogen atom, a carbon atom, an oxygen atom and a sulfur atom, R represents a polar substituent group or an organic group containing at least one of a thioether group, an amino group, an ammonium group, an ether group and a heterocyclic group, n represents 0 or 1 and m represents 1 or 2.

2. A process for forming a direct positive color image as claimed in claim 1, wherein the compound represented by the general formula (I) is a compound represented by the general formula (II).

General Formula (II)

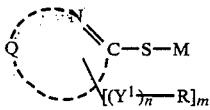

wherein, Q represents an atomic group required to form a 5- or 6-membered heterocyclic ring containing at least one atom selected from the group consisting of a carbon atom, a nitrogen atom, an oxygen atom, a sulfur atom, and a selenium atom, which may form a condensed ring together with an aromatic ring or heterocyclic ring, M represents a hydrogen atom, an alkali metal atom, an ammonium group or a group which can be replaced by H or an alkali metal atom under an alkaline condition, and $Y^1$, R, m and n are the same as those defined in claim 1.

3. A process for forming a direct positive color image as claimed in claim 1, wherein the compound represented by the general formula (I) is a compound represented by the general formula (III).

General formula (III)

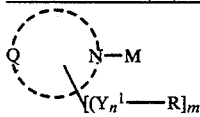

wherein, Q represents an atomic group required to form a 5- or 6-membered heterocyclic ring containing at least one atom selected from the group consisting of a carbon atom, a nitrogen atom, an oxygen atom, a sulfur atom, and a selenium atom, which may form a condensed ring together with an aromatic ring or heterocyclic ring, M represents a hydrogen atom, an alkali metal atom, an ammonium group or a group which can be replaced by H or an alkali metal atom under an alkaline condition, and $Y^1$, R, m and n are the under an same as those defined in claim 1.

4. A process for forming a direct positive color image as claimed in claim 2, wherein the compound represented by the general formula (II) is a compound represented by the general formula (IV)

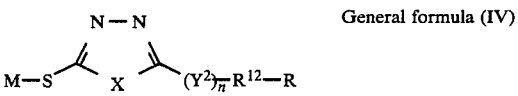    General formula (IV)

wherein, M represents a hydrogen atom, an alkali metal atom, an ammonium group, or a group which can cleave under an alkaline condition, X represents an oxygen atom, a sulfur atom or a selenium atom and $Y^2$ represents

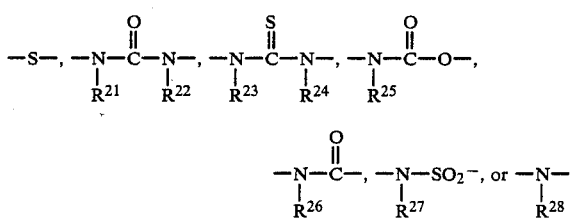

wherein $R^{21}$, $R^{22}$, $R^{24}$, $R^{25}$, $R^{26}$, $R^{27}$, and $R^{28}$ represents a hydrogen atom, a substituted or unsubstituted alkyl group, a substituted or unsubstituted aryl group, a substituted or unsubstituted alkenyl group, a substituted or unsubstituted aralkyl group, $R^{12}$ represents a straight or branched alkylene group, a straight or branched alkenylene group, a straight or branched aralkylene group, or an arylene group which may be further substituted, R represents a polar substituted group, and n represents 0 or 1.

5. A process for forming a direct positive color image as claimed in claim 2, wherein the compound represented by the general formula (II) is a compound represented by the general formula (V).

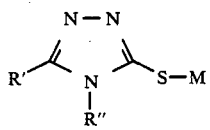    General formula (V)

wherein, R' represents a hydrogen atom, a halogen atom, a nitro group, a mercapto group or a $-(Y^3)_{\overline{n'}}R^{1-}$ 1—R group, R" represents a hydrogen atom or a $-(Y^4)_{\overline{m'}}R^{11}$—R group, at least one of R' and R" being $-(Y^3)_{\overline{n'}}R^{11}$—R and $-(Y^4)_{\overline{m'}}R^{11}$R, $Y^3$ and $Y^4$ each represents

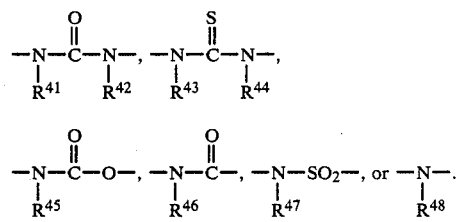

M represents a hydrogen atom, an alkali metal atom, an ammonium group, or a group which can cleave under an alkaline condition, $R^{41}$, $R^{42}$, $R^{43}$, $R^{44}$, $R^{45}$, $R^{46}$, $R^{47}$, and $R^{48}$ represents a hydrogen atom, a substituted or unsubstituted alkyl group, a substituted or unsubstituted aryl group, a substituted or unsubstituted alkenyl group, a substituted or unsubstituted aralkyl group, or $R^{17}$ represents a straight or branched alkylene group, a straight or branched alkenylene group, a straight or branched aralkylene group, or an arylene group, which may be further substituted, Z represents the same as those defined in the general formula (IV), n' represents 0 or 1 and m' represents 0 or 1.

6. A process for forming a direct positive color image as claimed in claim 4, wherein the compound represented by the general formula (II) is a compound represented by the general formula (VI)

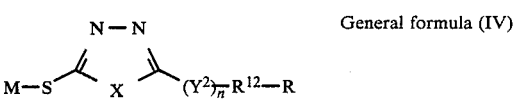    General formula (IV)

wherein, M represents a hydrogen atom, an alkali metal atom, an ammonium group, or a group which can cleave under an alkaline condition, X represents an oxygen atom, a sulfur atom or a selenium atom and $Y^2$ represents

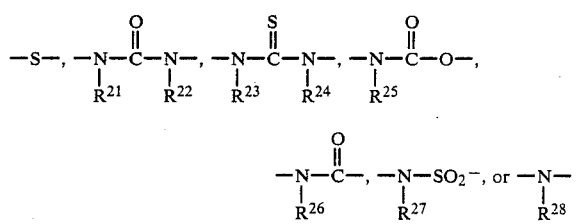

wherein $R^{21}$, $R^{22}$, $R^{24}$, $R^{25}$, $R^{26}$, $R^{27}$, and $R^{28}$ represents a hydrogen atom, a substituted or unsubstituted alkyl group, a substituted or unsubstituted aryl group, a substituted or unsubstituted alkenyl group, a substituted or unsubstituted aralkyl group, $R^{12}$ represents a straight or branched alkylene group, a straight or branched alkenylene group, a straight or branched aralkylene group, or an arylene group which may be further substituted, R represents a hydrogen atom, a halogen atom, a nitro group, a cyano group, a substituted or unsubstituted sulfonyl group, a carbamoyl group, a sulfamoyl group, a carbonamido group, a sulfonamido group, an acyloxy group, a ureido group, an acyl group, a thioureido group, a sulfonyloxy group, an oxycarbomyl group, an oxysulfonyl group and, or a mercapto group, and n represents 0 or 1.

* * * * *